United States Patent
Gliner et al.

(10) Patent No.: US 12,279,833 B2
(45) Date of Patent: *Apr. 22, 2025

(54) 2D PATHFINDER VISUALIZATION

(71) Applicant: Biosense Webster (Israel) Ltd., Yokneam (IL)

(72) Inventors: Vadim Gliner, Haifa (IL); Assaf Govari, Haifa (IL); Alon Boumendil, Givat Nili (IL); Yair Palti, Herzelia (IL); Remi Bettan, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 93 days.

This patent is subject to a terminal disclaimer.

(21) Appl. No.: 17/881,756

(22) Filed: Aug. 5, 2022

(65) Prior Publication Data
US 2023/0039532 A1    Feb. 9, 2023

Related U.S. Application Data

(63) Continuation of application No. 16/726,668, filed on Dec. 24, 2019, now Pat. No. 11,446,095.

(51) Int. Cl.
| | | |
|---|---|---|
| *A61B 34/20* | (2016.01) | |
| *A61B 6/03* | (2006.01) | |
| *A61B 6/46* | (2024.01) | |
| *G06T 7/30* | (2017.01) | |

(52) U.S. Cl.
CPC .............. *A61B 34/20* (2016.02); *A61B 6/032* (2013.01); *A61B 6/463* (2013.01); *G06T 7/30* (2017.01);
(Continued)

(58) Field of Classification Search
CPC ......... A61B 34/20; A61B 6/032; A61B 6/463; A61B 2034/2051; A61B 34/10;
(Continued)

(56) References Cited

U.S. PATENT DOCUMENTS

| | | |
|---|---|---|
| 5,371,778 A | 12/1994 | Yanof et al. |
| 9,974,525 B2 | 5/2018 | Weingarten et al. |
| (Continued) | | |

FOREIGN PATENT DOCUMENTS

| | | |
|---|---|---|
| JP | 2017-529116 A | 4/2021 |
| WO | WO 2016/004007 A1 | 1/2016 |

OTHER PUBLICATIONS

International Search Report and Written Opinion dated Mar. 1, 2021, for International Application No. PCT/IB2020/061006, 16 pages.
(Continued)

*Primary Examiner* — Joel Lamprecht
(74) *Attorney, Agent, or Firm* — Frost Brown Todd LLP

(57) ABSTRACT

In one embodiment, a medical apparatus, includes a medical instrument configured to move within a passage in a body of a patient, a position tracking system to track coordinates of the medical instrument within the body, a display screen, and a processor to register the position tracking system and a 3D computerized tomography (CT) image of at least a part of the body within a common frame of reference, find a 3D path of the medical instrument through the passage from a start point to a termination point within the common frame of reference, compute a direction to the 3D path from the medical instrument responsively to the tracked coordinates, and render and simultaneously display on the display screen respective 2D CT slices, based on the 3D CT image, including respective 2D indications of the direction to the 3D path from the instrument projected onto the respective 2D CT slices.

20 Claims, 21 Drawing Sheets

(52) U.S. Cl.
CPC ............... *A61B 2034/2051* (2016.02); *G06T 2207/10081* (2013.01); *G06T 2207/30004* (2013.01); *G06T 2207/30241* (2013.01)

(58) Field of Classification Search
CPC ...... A61B 2034/107; A61B 2034/2072; A61B 2090/364; A61B 34/25; G06T 7/30; G06T 2207/10081; G06T 2207/30004; G06T 2207/30241
See application file for complete search history.

(56) References Cited

U.S. PATENT DOCUMENTS

| | | | |
|---|---|---|---|
| 10,188,465 | B2 | 1/2019 | Gliner et al. |
| 10,872,449 | B2 | 12/2020 | Merlet et al. |
| 11,446,095 | B2 * | 9/2022 | Gliner ................. A61B 34/10 |
| 2005/0228250 | A1 | 10/2005 | Bitter et al. |
| 2006/0041181 | A1 | 2/2006 | Viswanathan et al. |
| 2007/0276214 | A1 | 11/2007 | Dachille et al. |
| 2008/0071141 | A1 | 3/2008 | Gattani et al. |
| 2011/0236868 | A1 | 9/2011 | Bronstein et al. |
| 2012/0184844 | A1 | 7/2012 | Gielen et al. |
| 2016/0174874 | A1 | 6/2016 | Averbuch et al. |
| 2017/0020411 | A1 | 1/2017 | Gliner et al. |
| 2017/0151027 | A1 | 6/2017 | Walker et al. |
| 2018/0303550 | A1 | 10/2018 | Altmann et al. |
| 2019/0046272 | A1 | 2/2019 | Zoabi et al. |

OTHER PUBLICATIONS

Japanese First Office Action dated Jun. 4, 2024, for Application No. 2022-538966, 5 pages.

* cited by examiner

2D PATHFINDER VISUALIZATION

This application is a continuation of U.S. application Ser. No. 16/726,668, filed Dec. 24, 2019, issued as U.S. Pat. No. 11,446,095, entitled "2D PATHFINDER VISUALIZATION."

FIELD OF THE INVENTION

The present invention relates to medical systems, and in particular, but not exclusively, to path visualization.

BACKGROUND

In image-guided surgery (IGS), a medical practitioner uses instruments that are tracked in real time within the body, so that positions and/or orientations of the instruments can be presented on images of a patient's anatomy during the surgical procedure. In many IGS scenarios an image of the patient is prepared in one modality, such as magnetic resonance imaging (MRI) or computerized tomography (CT), and the instrument tracking uses a different modality, such as electromagnetic tracking. In order for the tracking to be effective, frames of reference of the two modalities are registered with each other.

US Patent Publication 2011/0236868 of Bronstein, et al., issued as U.S. Pat. No. 10,580,325 on Mar. 3, 2020, describes a method of performing computerized simulations of image-guided procedures. The method may comprise receiving medical image data of a specific patient. A patient-specific digital image-based model of an anatomical structure of the specific patient may be generated based on the medical image data. A computerized simulation of an image-guided procedure may be performed using the digital image-based model. Medical image data, the image-based model and a simulated medical tool model may be simultaneously displayed.

US Patent Publication 2017/0151027 of Walker, et al., issued as U.S. Pat. No. 10,143,529 on Dec. 4, 2018, describes systems and methods for driving a flexible medical instrument to a target in an anatomical space with robotic assistance. The flexible instrument may have a tracking sensor embedded therein. An associated robotic control system may be provided, which is configured to register the flexible instrument to an anatomical image using data from the tracking sensor and identify one or more movements suitable for navigating the instrument towards an identified target. In some embodiments, the robotic control system drives or assists in driving the flexible instrument to the target.

US Patent Publication 2016/0174874 of Averbuch, et al., issued as U.S. Pat. No. 10,285,623 on May 14, 2019, describes a registration method whereby a sensor-based approach is used to establish initial registration and whereby upon the commencement of navigating an endoscope, image-based registration methods are used in order to more accurately maintain the registration between the endoscope location and previously-acquired images. A six-degree-of-freedom location sensor is placed on the probe in order to reduce the number of previously-acquired images that must be compared to a real-time image obtained from the endoscope.

US Patent Publication 2005/0228250 of Bitter, et al., now abandoned, describes a user interface including an image area that is divided into a plurality of views for viewing corresponding 2-dimensional and 3-dimensional images of an anatomical region. Tool control panes can be simultaneously opened and accessible. The segmentation pane enables automatic segmentation of components of a displayed image within a user-specified intensity range or based on a predetermined intensity.

US Patent Publication 2007/0276214 of Dachille, et al., now abandoned, describes an imaging system for automated segmentation and visualization of medical images and includes an image processing module for automatically processing image data using a set of directives to identify a target object in the image data and process the image data according to a specified protocol, a rendering module for automatically generating one or more images of the target object based on one or more of the directives and a digital archive for storing the one or more generated images. The image data may be DICOM-formatted image data), wherein the imaging processing module extracts and processes metadata in DICOM fields of the image data to identify the target object. The image processing module directs a segmentation module to segment the target object using processing parameters specified by one or more of the directives.

U.S. Pat. No. 5,371,778 to Yanof, et al., describes a CT scanner that non-invasively examines a volumetric region of a subject and generates volumetric image data indicative thereof. An object memory stores the data values corresponding to each voxel of the volume region. An affine transform algorithm operates on the visible faces of the volumetric region to translate the faces from object space to projections of the faces onto a viewing plane in image space. An operator control console includes operator controls for selecting an angular orientation of a projection image of the volumetric region relative to a viewing plane, i.e. a plane of the video display. A cursor positioning trackball inputs i- and j-coordinate locations in image space which are converted into a cursor crosshair display on the projection image. A depth dimension k between the viewing plane and the volumetric region in a viewing direction perpendicular to the viewing plane is determined. The (i,j,k) image space location of the cursor is operated upon by the reverse of the selected transform to identify a corresponding (x,y,z) cursor coordinate in object space. The cursor coordinate in object space is translated into corresponding addresses of the object memory for transverse, coronal, and sagittal planes through the volumetric region.

U.S. Pat. No. 10,188,465 to Gliner, et al., describes a method including receiving a computerized tomography scan of at least a part of a body of a patient, and identifying voxels of the scan that correspond to regions in the body that are traversable by a probe inserted therein. The method also includes displaying the scan on a screen and marking thereon selected start and termination points for the probe. A processor finds a path from the start point to the termination point consisting of a connected set of the identified voxels. The processor also uses the scan to generate a representation of an external surface of the body and displays the representation on the screen. The processor then renders an area of the external surface surrounding the path locally transparent in the displayed representation, so as to make visible on the screen an internal structure of the body in a vicinity of the path.

US Patent Publication 2018/0303550 of Altmann, et al., issued as U.S. Pat. No. 11,026,747 on Jun. 8, 2021, describes a method for visualization includes registering, within a common frame of reference, a position tracking system and a three-dimensional (3D) computerized tomography (CT) image of at least a part of a body of a patient. A location and orientation of at least one virtual camera are specified within the common frame of reference. Coordinates of a medical tool moving within a passage in the body are tracked using the position tracking system. A virtual endoscopic image, based on the 3D CT image, of the passage in the body is rendered and displayed from the specified location and orientation, including an animated representation of the medical tool positioned in the virtual endoscopic image in accordance with the tracked coordinates.

SUMMARY

There is provided in accordance with an embodiment of the present disclosure, a medical apparatus, including a medical instrument, which is configured to move within a passage in a body of a patient, a position tracking system, which is configured to track coordinates of the medical instrument within the body, a display screen, and a processor, which is configured to register the position tracking system and a three-dimensional (3D) computerized tomography (CT) image of at least a part of the body within a common frame of reference, find a 3D path of the medical instrument through the passage from a given start point to a given termination point within the common frame of reference, compute a direction to the 3D path from the medical instrument responsively to the tracked coordinates, and render and simultaneously display on the display screen respective two-dimensional (2D) CT slices, based on the 3D CT image, including respective 2D indications of the direction to the 3D path from the medical instrument projected onto the respective 2D CT slices.

Further in accordance with an embodiment of the present disclosure the respective 2D indications of the direction to the 3D path from the medical instrument include respective arrows.

Still further in accordance with an embodiment of the present disclosure the processor is configured to render and simultaneously display on the display screen the respective two-dimensional (2D) CT slices, based on the 3D CT image, including respective 2D indications of the direction to the 3D path from the medical instrument projected into the respective 2D CT slices, and a representation of the medical instrument responsively to the tracked coordinates.

Additionally, in accordance with an embodiment of the present disclosure the processor is configured to compute a direction to a closest point of the 3D path from the medical instrument responsively to the tracked coordinates.

Moreover, in accordance with an embodiment of the present disclosure the processor is configured to compute a 3D vector to the 3D path from the medical instrument responsively to the tracked coordinates.

Further in accordance with an embodiment of the present disclosure the processor is configured to render and simultaneously display on the display screen the respective 2D CT slices, based on the 3D CT image, including the respective 2D indications of the 3D vector to the 3D path from the medical instrument projected onto the respective 2D CT slices.

Still further in accordance with an embodiment of the present disclosure the processor is configured to render and simultaneously display on the display screen three respective two-dimensional (2D) CT slices, based on the 3D CT image, including three respective 2D indications of the direction to the 3D path from the medical instrument projected onto the three respective 2D CT slices.

Additionally, in accordance with an embodiment of the present disclosure the three respective 2D slices respectively include a Coronal view, a Sagittal view, and a Transversal view.

Moreover in accordance with an embodiment of the present disclosure the processor is configured to compute a distance to the 3D path from the medical instrument responsively to the tracked coordinates, and render and simultaneously display on the display screen the respective two-dimensional (2D) CT slices, based on the 3D CT image, including respective 2D indications of the direction and the distance to the 3D path from the medical instrument projected onto the respective 2D CT slices.

Further in accordance with an embodiment of the present disclosure the processor is configured to render and simultaneously display on the display screen the respective two-dimensional (2D) CT slices, based on the 3D CT image, including the respective 2D indications of the direction to the 3D path from the medical instrument projected onto the respective 2D CT slices, and a virtual endoscopic image, based on the 3D CT image, of the passage in the body viewed from at least one respective location of at least one respective virtual camera including an animated representation of the medical instrument positioned in the virtual endoscopic image in accordance with the tracked coordinates, and a 3D indication of the direction to the 3D path from the medical instrument.

Still further in accordance with an embodiment of the present disclosure the position tracking system includes an electromagnetic tracking system, which includes one or more magnetic field generators positioned around the part of the body and a magnetic field sensor at a distal end of the medical instrument.

There is also provided in accordance with another embodiment of the present disclosure, a medical method, including tracking coordinates of a medical instrument within a body of a patient using a position tracking system, the medical instrument being configured to move within a passage in the body of the patient, registering the position tracking system and a three-dimensional (3D) computerized tomography (CT) image of at least a part of the body within a common frame of reference, finding a 3D path of the medical instrument through the passage from a given start point to a given termination point within the common frame of reference, computing a direction to the 3D path from the medical instrument responsively to the tracked coordinates, and rendering and simultaneously displaying on a display screen respective two-dimensional (2D) CT slices, based on the 3D CT image, including respective 2D indications of the direction to the 3D path from the medical instrument projected onto the respective 2D CT slices.

Additionally, in accordance with an embodiment of the present disclosure the respective 2D indications of the direction to the 3D path from the medical instrument include respective arrows.

Moreover, in accordance with an embodiment of the present disclosure the rendering and simultaneously displaying includes rendering and simultaneously displaying on the display screen the respective two-dimensional (2D) CT slices, based on the 3D CT image, including respective 2D indications of the direction to the 3D path from the medical instrument projected into the respective 2D CT slices, and a representation of the medical instrument responsively to the tracked coordinates.

Further in accordance with an embodiment of the present disclosure the computing includes computing a direction to a closest point of the 3D path from the medical instrument responsively to the tracked coordinates.

Still further in accordance with an embodiment of the present disclosure the computing includes computing a 3D vector to the 3D path from the medical instrument responsively to the tracked coordinates.

Additionally, in accordance with an embodiment of the present disclosure the rendering and simultaneously displaying includes rendering and simultaneously displaying on the display screen the respective 2D CT slices, based on the 3D CT image, including the respective 2D indications of the 3D vector to the 3D path from the medical instrument projected onto the respective 2D CT slices.

Moreover, in accordance with an embodiment of the present disclosure the rendering and simultaneously displaying includes rendering and simultaneously displaying on the display screen three respective two-dimensional (2D) CT slices, based on the 3D CT image, including three respective 2D indications of the direction to the 3D path from the medical instrument projected onto the three respective 2D CT slices.

Further in accordance with an embodiment of the present disclosure the three respective 2D slices respectively include a Coronal view, a Sagittal view, and a Transversal view.

Still further in accordance with an embodiment of the present disclosure, the method includes computing a distance to the 3D path from the medical instrument responsively to the tracked coordinates, and wherein the rendering and simultaneously displaying includes rendering and simultaneously displaying on the display screen the respective two-dimensional (2D) CT slices, based on the 3D CT image, including respective 2D indications of the direction and the distance to the 3D path from the medical instrument projected onto the respective 2D CT slices.

Additionally, in accordance with an embodiment of the present disclosure the rendering and simultaneously displaying includes rendering and simultaneously displaying on the display screen the respective two-dimensional (2D) CT slices, based on the 3D CT image, including the respective 2D indications of the direction to the 3D path from the medical instrument projected onto the respective 2D CT slices, and a virtual endoscopic image, based on the 3D CT image, of the passage in the body viewed from at least one respective location of at least one respective virtual camera including an animated representation of the medical instrument positioned in the virtual endoscopic image in accordance with the tracked coordinates, and a 3D indication of the direction to the 3D path from the medical instrument.

There is also provided in accordance with still another embodiment of the present disclosure a software product, including a non-transient computer-readable medium in which program instructions are stored, which instructions, when read by a central processing unit (CPU), cause the CPU to track coordinates of a medical instrument within a body of a patient using a position tracking system, the medical instrument being configured to move within a passage in the body of the patient, register the position tracking system and a three-dimensional (3D) computerized tomography (CT) image of at least a part of the body within a common frame of reference, find a 3D path of the medical instrument through the passage from a given start point to a given termination point within the common frame of reference, compute a direction to the 3D path from the medical instrument responsively to the tracked coordinates, and render and simultaneously display on a display screen respective two-dimensional (2D) CT slices, based on the 3D CT image, including respective 2D indications of the direction to the 3D path from the medical instrument projected onto the respective 2D CT slices.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
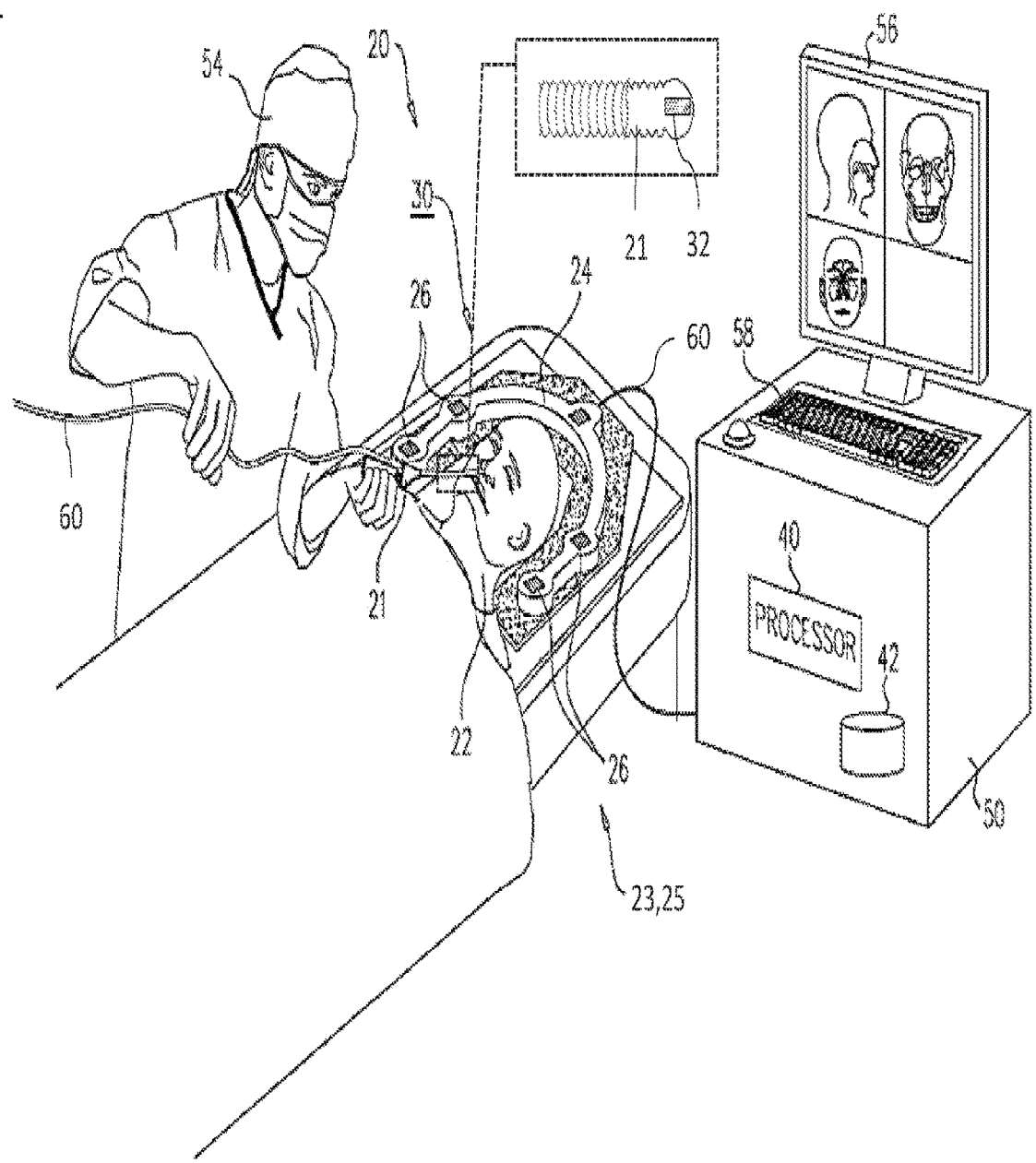
FIG. 1 is a partly pictorial, partly block diagram view of a medical system constructed and operative in accordance with an embodiment of the present invention.

During medical procedures within the nasal passages, such as sinuplasty operations, it is impossible to directly visualize what is happening without insertion of an endoscope into the sinuses. Insertion of an endoscope is problematic, however, because of the tight spaces involved, as well as the extra cost of the endoscope. Furthermore, endoscopes for use in the nasal passages are typically rigid instruments, which cannot make turns or provide views from sinus cavities back toward the sinus opening.

Embodiments of the present invention that are described herein address this problem by generating virtual endoscopic views of the procedure from virtual cameras, similar to what would be seen by an actual endoscope positioned at the locations of the virtual cameras within the nasal passages. The virtual endoscopic views show the anatomy as well as the medical instrument moving through the anatomy. As the medical instrument moves along a passage, the virtual cameras used to generate the virtual endoscopic views passes from one virtual camera to the other responsively to tracked coordinates of the medical instrument.

These virtual endoscope views may be used, for example, in visualizing the location and orientation of a guidewire relative to the anatomy, as well as other instruments, such as a suction tool or a shaving tool (debrider).

Moving from one virtual camera to the other provides a more stable view of the anatomy than placing a virtual camera on the distal tip of the medical instrument whereby the virtual camera is always "moving" as the distal tip moves leading to a jumpy or choppy video of the anatomy which is very difficult to follow.

Furthermore, although the embodiments disclosed hereinbelow are directed specifically to visualization within the nasal passages, the principles of the present invention may similarly be applied within other spaces in the body, particularly in narrow passages in which actual optical endoscopy is unavailable or difficult to use.

Prior to the medical procedure, a CT image of the patient's head, including the sinuses, is acquired, and a position tracking system, such as an electromagnetic tracking system, is registered with the CT image. A position sensor is attached to the distal end of the guidewire or other instrument, and the distal end is thus tracked, in location and orientation, relative to the registered CT image, as it is inserted into the sinuses. The CT image of the head is processed in order to generate and display images of the 3D volume of the nasal passages.

Inside this 3D volume, an operator of the imaging system, such as a surgeon performing a sinuplasty procedure, can select start and termination points of a 3D path along which to navigate the medical instrument. A suitable 3D path from the start to the termination point is computed, for example, using a path finding algorithm and data from the CT image indicating which voxels of the CT image include material suitable for traversing, such as air or liquid.

The computed 3D path is automatically divided into segments with turning points between the segments above a threshold turning value. The virtual cameras are positioned around these turning points. Additional virtual cameras may be automatically positioned between the turning points if there is no line of sight between the virtual cameras positioned at the turning points and/or if the distance between the turning points exceeds a given value.

The orientation of the optical axis of each virtual camera is computed. The orientation may be computed using any suitable method. In some embodiments, the orientation may be computed based on an average direction of vectors from a virtual camera to locations along the path until the next virtual camera. In other embodiments, the orientation may be computed as a direction parallel to the path at the location of the respective virtual camera. The field of view of the virtual cameras may be fixed, e.g., to 90 degrees or any suitable value, or set according to the outer limits of the relevant segment of the path served by the respective virtual cameras with an additional tolerance to allow for deviations from the path.

In some embodiments, the location of a virtual camera may be shifted backwards in an opposite direction to the computed average direction. The virtual camera may be shifted back by any suitable distance, for example, until the camera is shifted back to solid material such as tissue or bone. Shifting the virtual cameras back may result in a better view of the medical instrument within the respective virtual endoscopic images particularly when the medical instrument is very close to the respective virtual cameras, and may result in a better view of the surrounding anatomy.

As the medical tool moves through the passages, the respective virtual cameras are selected for rendering and displaying respective virtual endoscopic images according to a camera selection method. In some embodiments, the camera selection method includes finding a closest camera to the tracked coordinates of the medical instrument and then finding which side of a bisector (plane) associated with the closest camera the tracked coordinates fall. If the tracked coordinates fall on the side of the bisector further down the computed path (in the direction of travel of the medical instrument) from the closest camera, the closest camera is selected for rendering. If the tracked coordinates fall on the side of the bisector closest to the current virtual camera, the current virtual camera continues to provide its endoscopic image. The bisector associated with the closest camera may be defined as a plane perpendicular to the computed path at the point of the closest camera. In other embodiments, the passages may be divided into regions based on the segments with the virtual cameras being selected according to the region in which the tracked coordinates are disposed.

The transition between two virtual cameras and therefore the transition between the associated virtual endoscopic images may be a smooth transition or a sharp transition. In some embodiments, a smooth transition between the two respective virtual cameras may be performed by finding locations of addition virtual cameras on the path between the two the virtual cameras and then successively rendering respective transitional virtual endoscope images viewed from the locations of the additional virtual cameras.

Although 3D images may be used to help a physician navigate a medical instrument along a computed path, some physicians are not comfortable with a 3D image presentation for this purpose.

Embodiments of the present invention solve the above problem by rendering and displaying, on a display, two-dimensional (2D) CT slices of a CT image, such as 2D Coronal, Sagittal, and Transversal slices of a 3D CT image showing on each 2D image a direction in which to move the medical instrument in order to return the medical instrument to the computed path. In some embodiments, a 3D image, such as a virtual endoscopic image, showing a representation of the medical tool may be displayed alongside the 2D CT slices.

In some embodiments, a processor computes a direction, and optionally a distance, and/or a 3D vector, to the 3D path (e.g., to a closest point on the 3D path) from the medical instrument responsively to the tracked coordinates of the medical instrument. The processor renders and simultaneously displays on the display screen respective 2D CT slices, based on a 3D CT image, including respective 2D indications (e.g., arrows or other symbols) of the direction, and optionally the distance, and/or the 3D vector, to the 3D path from the medical instrument projected onto the respective 2D CT slices, and optionally a representation of the medical instrument responsively to the tracked coordinates. In some embodiments, the respective 2D slices respectively include a Coronal view, a Sagittal view, and a Transversal view.

System Description

Reference is now made to FIG. 1, which is a partly pictorial, partly block diagram view of a medical apparatus 20 constructed and operative in accordance with an embodiment of the present invention. In the following description a medical instrument 21 of apparatus 20 is assumed to be used to perform a medical procedure on a patient 22. The medical instrument 21 is configured to move within a passage in a body of the patient 22.

The medical apparatus 20 includes a position tracking system 23, which is configured to track coordinates of the medical instrument 21 within the body. In some embodiments, the position tracking system 23 comprises an electromagnetic tracking system 25, which comprises one or more magnetic field generators 26 positioned around the part of the body and one or more magnetic field sensors 32 at a distal end of the medical instrument 21. In one embodiment, the magnetic field sensors 32 comprises a single axis coil and a dual axis coil which act as magnetic field sensors and which are tracked during the procedure by the electromagnetic tracking system 25. For the tracking to be effective, in apparatus 20 frames of reference of a CT (computerized tomography) image of patient 22 and of the electromagnetic tracking system 25 are registered described in more detail with reference to FIGS. 2 and 3. While the CT image may typically comprise a magnetic resonance imaging (MRI) image or a fluoroscopic image, in the description herein the image is assumed to comprise, by way of example, a fluoroscopic CT image. In some embodiments, the position tracking system 23 may track coordinates of the medical instrument 21 using any suitable tracking method, for example, based on current or impedance distributions over body surface electrodes, or based on ultrasound transducers.

Prior to and during the sinus procedure, a magnetic radiator assembly 24, comprised in the electromagnetic tracking system 25, is positioned beneath the patient's head. The magnetic radiator assembly 24 comprises the magnetic field generators 26 which are fixed in position and which transmit alternating magnetic fields into a region 30 wherein the head of patient 22 is located. Potentials generated by the single axis coil of the magnetic field sensor(s) 32 in region 30, in response to the magnetic fields, enable its position and its orientation to be measured in the magnetic tracking system's frame of reference. The position can be measured in three linear dimensions (3D), and the orientation can be measured for two axes that are orthogonal to the axis of symmetry of the single axis coil. However, the orientation of the single axis coil with respect to its axis of symmetry cannot be determined from the potentials generated by the coil.

The same is true for each of the two coils of the dual axis coil of the magnetic field sensor 32. That is, for each coil the position in 3D can be measured, as can the orientation with respect to two axes that are orthogonal to the coil axis of symmetry, but the orientation of the coil with respect to its axis of symmetry cannot be determined.

By way of example, radiators 26 of assembly 24 are arranged in an approximately horseshoe shape around the head of patient 22. However, alternate configurations for the radiators of assembly 24 will be apparent to those having skill in the art, and all such configurations are assumed to be comprised within the scope of the present invention.

Prior to the procedure, the registration of the frames of reference of the magnetic tracking system with the CT image may be performed by positioning a magnetic sensor at known positions, such as the tip of the patient's nose, of the image. However, any other convenient system for registration of the frames of reference may be used as described in more detail with reference to FIG. 2.

Elements of apparatus 20, including radiators 26 and magnetic field sensor 32, are under overall control of a system processor 40. Processor 40 may be mounted in a console 50, which comprises operating controls 58 that typically include a keypad and/or a pointing device such as a mouse or trackball. Console 50 connects to the radiators and to the magnetic field sensor 32 via one or more cables 60 and/or wirelessly. A physician 54 uses operating controls 58 to interact with the processor 40 while performing the medical procedure using apparatus 20. While performing the procedure, the processor may present results of the procedure on a display screen 56.

Processor 40 uses software stored in a memory 42 to operate apparatus 20. The software may be downloaded to processor 40 in electronic form, over a network, for example, or it may, alternatively or additionally, be provided and/or stored on non-transitory tangible media, such as magnetic, optical, or electronic memory.

Figure 2:
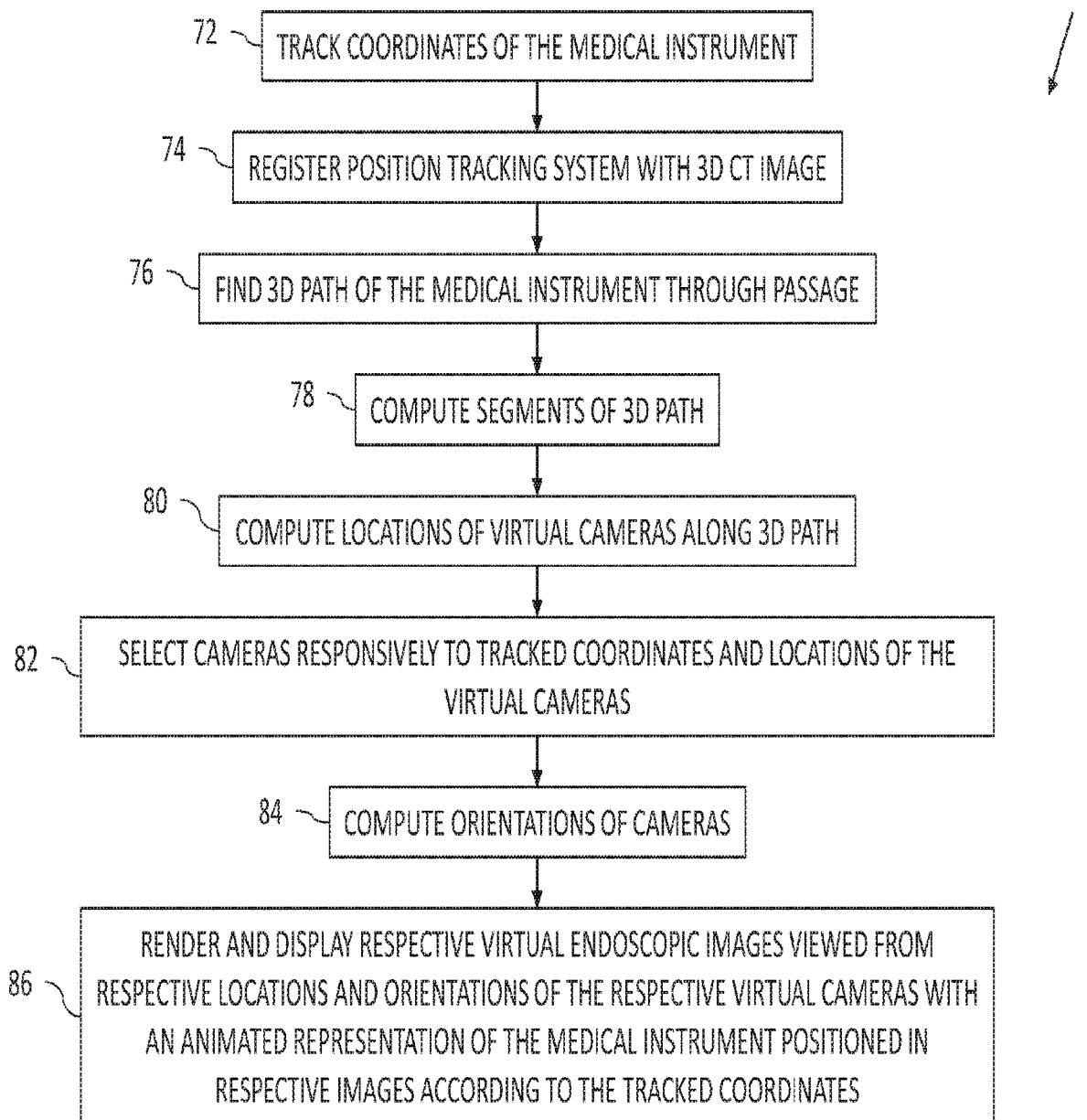
FIG. 2 is a flowchart including steps in a method of three-dimensional path visualization for use in the apparatus of FIG. 1 in accordance with an embodiment of the present invention.

Reference is now made to FIG. 2, which is a flowchart 70 including steps in a method of three-dimensional path visualization for use in the apparatus 20 of FIG. 1 in accordance with an embodiment of the present invention.

The position tracking system 23 (FIG. 1) is configured to track (block 72) coordinates of the distal end of the medical instrument 21 (FIG. 1) within the body. The processor 40 (FIG. 1) is configured to register (block 74) the position tracking system 23 and a three-dimensional (3D) computerized tomography (CT) image of at least a part of the body within a common frame of reference. The registration may be performed by any suitable registration technique. For example, but not limited to, a registration method described in U.S. Patent Publication 2017/0020411, issued as U.S. Pat. No. 10,638,954 on May 5, 2020, or 2019/0046272, issued as U.S. Pat. No. 11,986,252 on May 21, 2024. As described in the latter patent publication, for example, processor 40 may analyze the CT image to identify respective locations of the patient's eyes in the image, thus defining a line segment joining these respective locations. In addition, processor 40 identifies a voxel subset in the CT that overlies bony sections of the head, along a second line segment parallel to the first line segment and a third line segment perpendicular to the first line segment. The physician 54 positions a probe in proximity to the bony sections and thus measures positions on the surface of the head overlying the bony sections. Processor 40 computes the correspondence between these measured positions and the voxel subset in the CT image and thus registers the magnetic tracking system 25 with the CT image.

The processor 40 is configured to find (block 76) a 3D path of the medical instrument 21 through a passage from a given start point to a given termination point. The step of block 76 is described in more detail with reference to the path finding method of FIGS. 3-9.

The processor 40 is configured to compute (block 78) segments of the computed 3D path. The processor 40 is configured to compute (block 80) respective different locations along the 3D path of respective virtual cameras responsively to the computed segments. The steps of blocks 78 and 80 are described in more detail with reference to FIGS. 10-12.

The processor 40 is configured to select (block 82) the respective virtual cameras for rendering respective virtual endoscopic images responsively to the tracked coordinates of the medical instrument 21 and the respective locations of the respective virtual cameras within the common frame of reference. As the medical instrument 21 moves along the 3D path (which may be some distance either side of the path as the medical instrument 21 is not locked to the path), the virtual camera providing the virtual endoscopic image is selected according to the tracked coordinates of the medical instrument 21 and control is passed successively from one virtual camera to another as the medical instrument 21 moves along the path. The step of block 82 may be repeated intermittently, for example, each time new tracked coordinates are received, for example, in a range between 10 and 100 milliseconds, such as 50 milliseconds. The step of block 82 is described in more detail with reference to FIGS. 13-15.

The processor 40 is configured to compute (block 84) respective orientations of the respective virtual cameras. The orientation of the cameras is generally a 3D orientation and is defined with respect to a respective optical axis of the respective virtual cameras. In other words, the orientation of the cameras is a measure of which directions the cameras are facing for optical purposes. The location of the virtual cameras may also be shifted back as described in more detail with reference to FIGS. 16 and 18. The orientations and/or the shifting back may be computed before a camera is selected, as part of the process of selecting a camera, or when the medical instrument 21 leaves the field of view of the virtual camera currently providing the virtual endoscopic image.

The processor 40 is configured to render and display (block 86) on the display screen 56 (FIG. 1) the respective virtual endoscopic images, based on the 3D CT image, of the passage in the body viewed from the respective locations and orientations of the respective virtual cameras including an animated representation of the medical instrument 21 positioned in the respective virtual endoscopic images in accordance with the tracked coordinates. In other words, based on the location and orientation of the medical instrument 21 and the pre-acquired CT data, the processor 40 renders respective images as they would be captured by the respective virtual cameras and presents the images on the display screen 56, at the step of block 86. The image rendered by any given selected virtual camera is a projection of a portion of the 3D volume that would be visible from the camera location onto the virtual image plane of the camera. The step of block 86 is described in more detail with reference to FIGS. 21-23.

Figure 3:
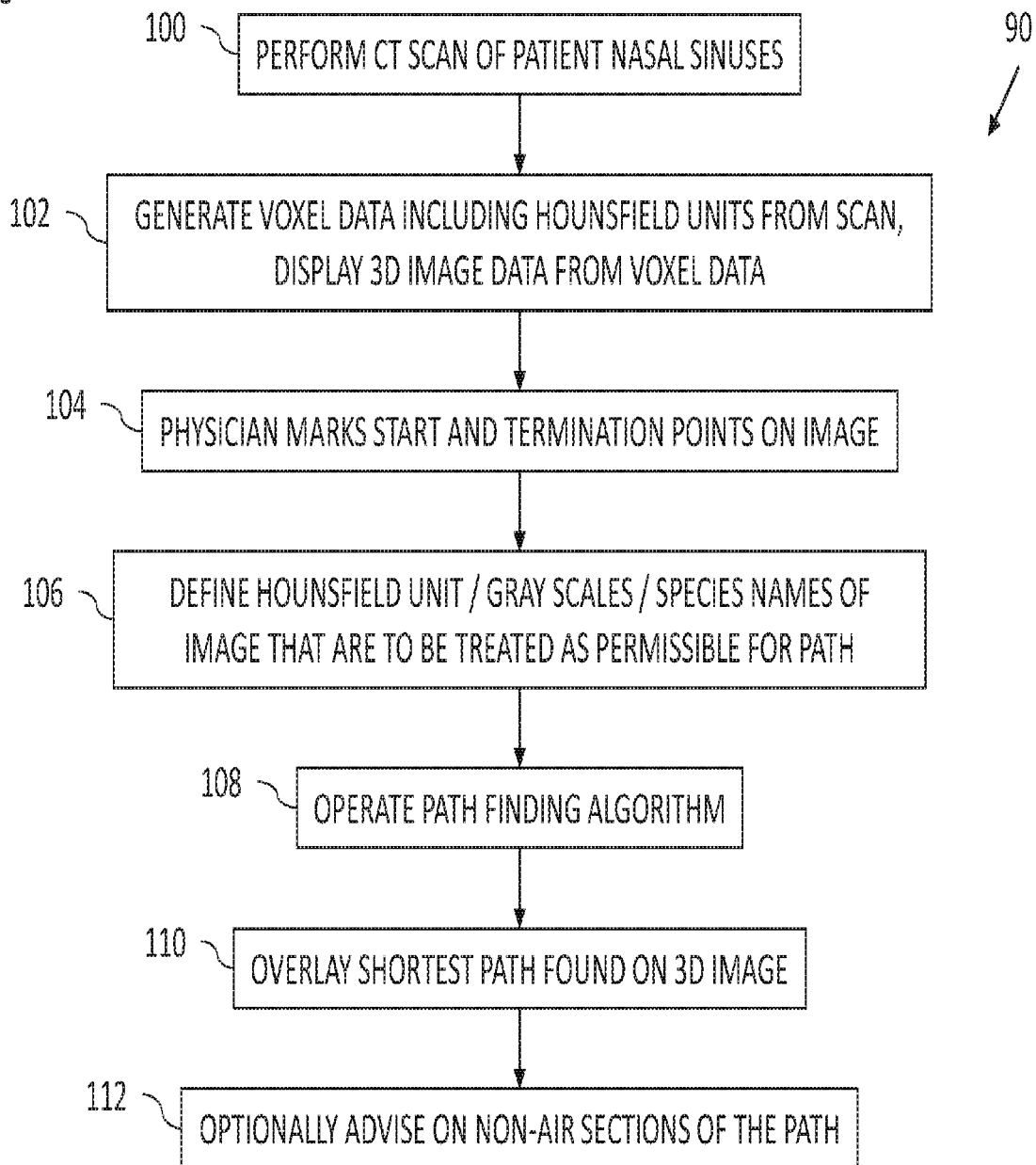
FIG. 3 is a flowchart including steps of a method of finding a path through a passage using the apparatus of FIG. 1.

Reference is now made to FIG. 3, which is a flowchart 90 including steps of a method of finding a path through a passage using the apparatus 20 of FIG. 1. FIGS. 4-9 are schematic diagrams illustrating the steps of the method of the flowchart of FIG. 3. The pre-planning component described with reference to the flowchart 90 is typically implemented prior to performance of the invasive surgery procedure on patient 22 (FIG. 1), and determines an optimal path to be followed by invasive medical instrument 21 (FIG. 1) in the procedure. The pre-planning is assumed to be performed by physician 54 (FIG. 1).

In an initial step (block 100 of the flowchart 90), a computerized tomography (CT) X-ray scan of the nasal sinuses of patient 22 is performed, and the data from the scan is acquired by processor 40. As is known in the art, the scan comprises two-dimensional X-ray "slices" of the patient 22, and the combination of the slices generates three-dimensional voxels, each voxel having a Hounsfield unit, a measure of radiodensity, determined by the CT scan.

In an image generation step (block 102), physician 54 (FIG. 1) displays results of the scan on display screen 56 (FIG. 1). As is known in the art, the results may be displayed as a series of two-dimensional (2D) slices, typically along planes parallel to the sagittal, coronal, and/or transverse planes of patient 22, although other planes are possible. The direction of the planes may be selected by the physician 54.

Figure 4:
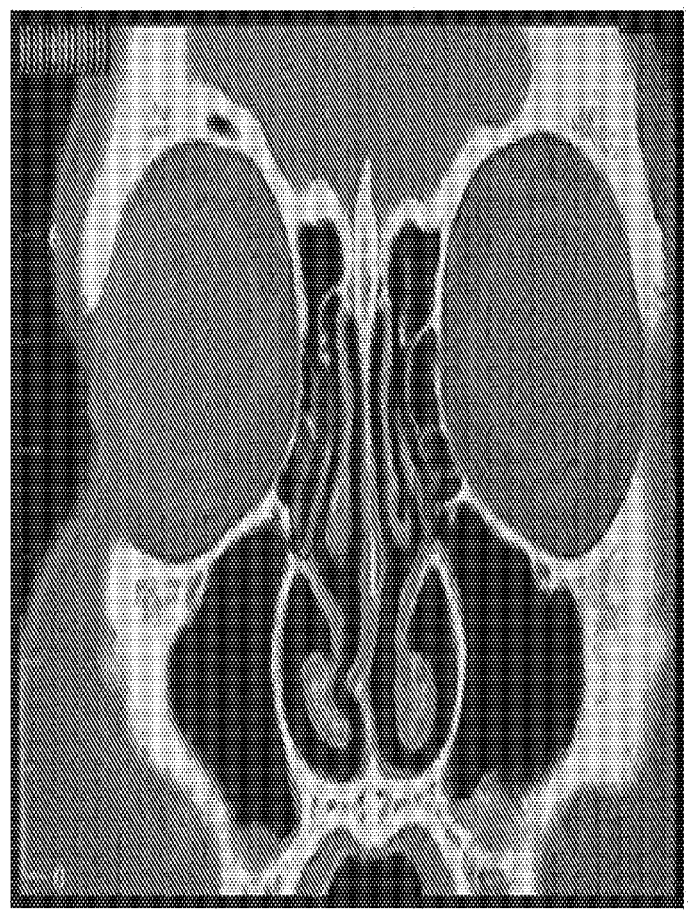
FIGS. 4-9 are schematic diagrams illustrating the steps of the method if the flowchart of FIG. 3.

The displayed results are typically gray scale images, and an example is provided in FIG. 4, which is a slice parallel to the coronal plane of patient 22. The values of the gray scales, from black to white, may be correlated with the Hounsfield unit (HU) of the corresponding voxels, so that, as applies to the image of FIG. 4, air having HU=−1000 may be assigned to be black, and dense bone having HU=3000 may be assigned to be white.

As is known in the art, apart from the values for air and water, which by definition are respectively −1000 and 0, the value of the Hounsfield unit of any other substance or species, such as dense bone, is dependent, inter alia, on the spectrum of the irradiating X-rays used to produce the CT scans referred to herein. In turn, the spectrum of the X-rays depends on a number of factors, including the potential in kilovolts (kV) applied to the X-ray generator, as well as the composition of the anode of the generator. For clarity in the present disclosure, the values of Hounsfield units for a particular substance or species are assumed to be as given in Table I below.

| Species/Substance | Hounsfield Unit |
| --- | --- |
| Air | −1000 |
| Soft Tissue | −300 to −100 |
| Fat | −50 |
| Water | 0 |
| Blood | +30 to +45 |
| Dense Bone | +3000 |

However the numerical values of HUs for particular species (other than air and water) as given in Table I are to be understood as being purely illustrative, and those having ordinary skill in the art will be able to modify these illustrative values, without undue experimentation, according to the species and the X-ray machine used to generate the CT images referred to herein.

Typically, a translation between HU values and gray scale values is encoded into a DICOM (Digital Imaging and Communications in Medicine) file that is the CT scan output from a given CT machine. For clarity in the following description the correlation of HU=−1000 to black, and HU=3000 to white, and correlations of intermediate HU values to corresponding intermediate gray levels is used, but it will be understood that this correlation is purely arbitrary. For example, the correlation may be "reversed," i.e., HU=−1000 may be assigned to white, HU=3000 assigned to black, and intermediate HU values assigned to corresponding intermediate gray levels. Thus, those having ordinary skill in the art will be able to adapt the description herein to accommodate other correlations between Hounsfield units and gray levels, and all such correlations are assumed to be comprised within the scope of the present invention.

In a marking step (block 104) the physician 54 (FIG. 1) marks an intended start point, where he/she will insert medical instrument 21 (FIG. 1) into the patient 22 (FIG. 1), and an intended termination point, where the distal end of the medical instrument 21 is to terminate. The two points may be on the same 2D slice. Alternatively, each point may be on a different slice. Typically, but not necessarily, both points are in air, i.e., where HU=−1000, and the termination point is usually, but not necessarily, at a junction of air with liquid or tissue shown in the slice. An example where the termination point is not at such a junction is when the point may be in the middle of an air-filled chamber.

Figure 5:
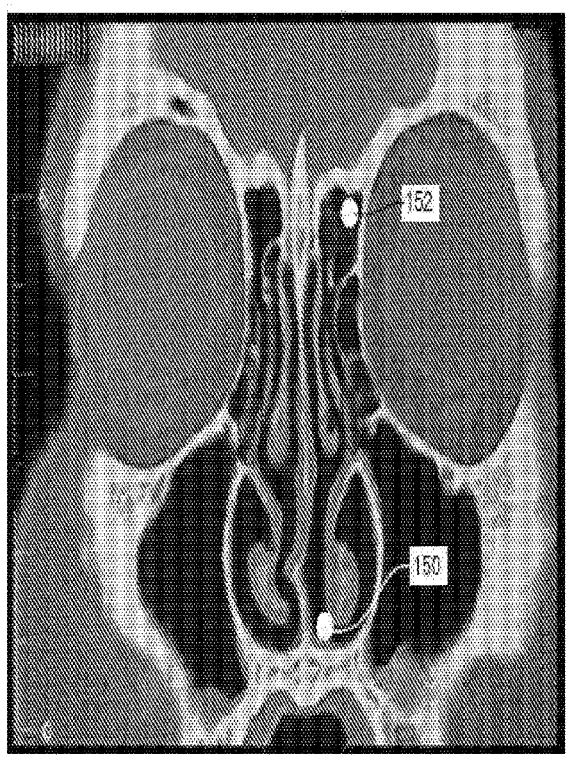

FIG. 5 illustrates a start point 150 and a termination point 152 that are marked on the same 2D slice by the physician, and for clarity these points are assumed, except where otherwise stated, to be the points used in the remaining description of the flowchart. Typically, the start and termination points are displayed in a non-gray scale color, for example, red.

In a permissible path definition step (block 106), the physician defines ranges of Hounsfield units which the path finding algorithm, referred to below, uses as acceptable voxel values in finding a path from start point 150 to termination point 152. The defined range typically includes HUs equal to −1000, corresponding to air or a void in the path; the defined range may also include HUs greater than −1000, for example, the range may be defined as given by expression (1):

$$\{HU|-1000 \leq HU \leq U\} \quad (1)$$

where U is a value selected by the physician.

For example, U may be set to +45, so that the path taken may include water, fat, blood, soft tissue as well as air or a void. In some embodiments, the range may be set by the processor 40 (FIG. 1) without intervention of the physician.

There is no requirement that the defined range of values is a continuous range, and the range may be disjoint, including one or more sub-ranges. In some embodiments a sub-range may be chosen to include a specific type of material. An example of a disjoint range is given by expression (2):

$$\{HU|HU=-1000 \text{ or } A \leq HU \leq B\} \quad (2)$$

where A, B are values selected by the physician.

For example, A and B may be set to be equal to −300 and −100 respectively, so that the path taken may include air or a void and soft tissue.

The method of selection for the range of HUs may include any suitable method, including, but not being limited to, by number, and/or by name of material, and/or by gray scale. For example, in the case of selection by gray scale, physician 54 (FIG. 1) may select one or more regions of the CT image, and the HU equivalents of the gray scale values of the selected regions are included in the acceptable range of HUs for voxels of the path to be determined by the path finding algorithm.

In the case of selection by name, a table of named species may be displayed to the physician. The displayed table is typically similar to Table I, but without the column providing values of Hounsfield units. The physician may select one or more named species from the table, in which case the HU equivalents of the selected named species are included in the acceptable range of HUs for voxels of the path to be determined by the path finding algorithm.

In a path finding step (block 108), processor 40 (FIG. 1) implements a path finding algorithm to find one or more shortest paths, between start point 150 and termination point 152, that is to be followed by medical instrument 21 (FIG. 1). The algorithm assumes that traversable voxels in the path include any voxels having HUs in the HU range defined in the step of block 106, and that voxels having HU values outside this defined range act as barriers in any path found. While the path finding algorithm used may be any suitable algorithm that is able to determine a shortest path within a three-dimensional maze, the inventors have found that the Flood Fill algorithm, Dijkstra's algorithm, or an extension such as the A* algorithm, give better results in terms of speed of computation and accuracy of determining the shortest path than other algorithms such as Floyd's algorithm or variations thereof.

In some embodiments, the path finding step includes taking account of mechanical properties and dimensions of medical instrument 21 (FIG. 1). For example, in a disclosed embodiment, medical instrument 21 may be limited, when it bends, to a range of possible radii of curvature. In determining possible paths to be followed by the medical instrument 21, the processor 40 (FIG. 1) ensures that no portion of the path defines a radius less than this range of radii.

In a further disclosed embodiment, the processor 40 (FIG. 1) takes account of mechanical properties of the medical instrument 21 (FIG. 1) that permit different portions of the medical instrument 21 different ranges of radii of curvature. For example, the end of a possible path may have a smaller radius of curvature than the possible radii of curvature of a proximal part of the medical instrument 21. However, the distal end of the medical instrument 21 may be more flexible than the proximal part, and may be flexible enough to accommodate the smaller radius of curvature, so that the possible path is acceptable.

In considering the possible radii of curvature of the medical instrument 21 (FIG. 1), and the different radii of curvature of possible paths, the processor 40 (FIG. 1) takes into account which portions of a path need to be traversed by different portions of the medical instrument 21, and the radii of curvature achievable by the medical instrument 21, as the distal end of the medical instrument 21 moves from start point 150 to termination point 152.

In a yet further disclosed embodiment, the processor 40 (FIG. 1) ensures that a path diameter D is always larger than a measured diameter d of medical instrument 21. The confirmation may be at least partially implemented, for example, by the processor 40 using erosion/dilation algorithms, as are known in the art, to find voxels within the ranges defined in the step of block 106.

Figure 6:
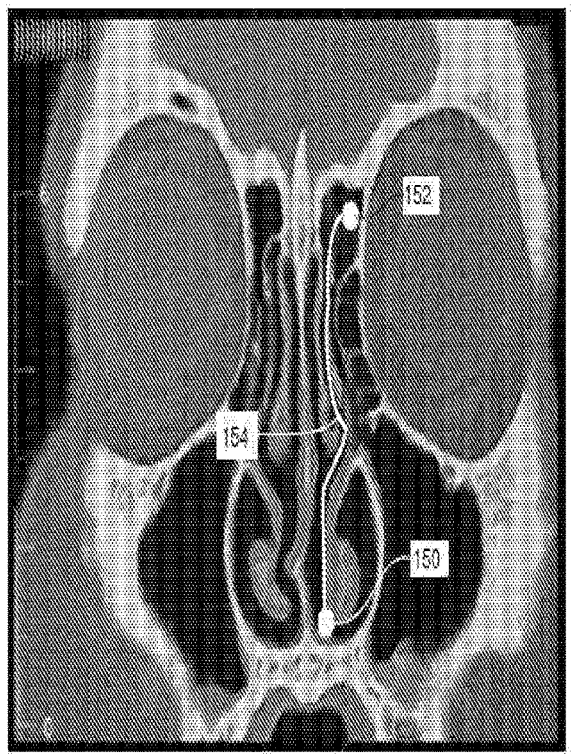

In an overlay step (block 110), the shortest path found in the step of block 108 is overlaid on an image that is displayed on display screen 56. FIG. 6 illustrates a shortest path 154, between start point 150 and termination point 152, that has been overlaid on the image of FIG. 5. Typically path 154 is displayed in a non-gray scale color, which may or may not be the same color as the start and termination points. In the case that the step of block 108 finds more than one shortest path, all such paths may be overlaid on the image, typically in different non-gray scale colors.

Typically, the path found traverses more than one 2D slice, in which case the overlaying may be implemented by incorporating the path found into all the 2D slices that are relevant, i.e., through which the path traverses. Alternatively, or additionally, an at least partially transparent 3D image may be generated from the 2D slices of the scan, and the path found may be overlaid on the 3D image. The at least partially transparent 3D image may be formed on a representation of an external surface of patient 22, as is described in more detail below.

Figure 7:
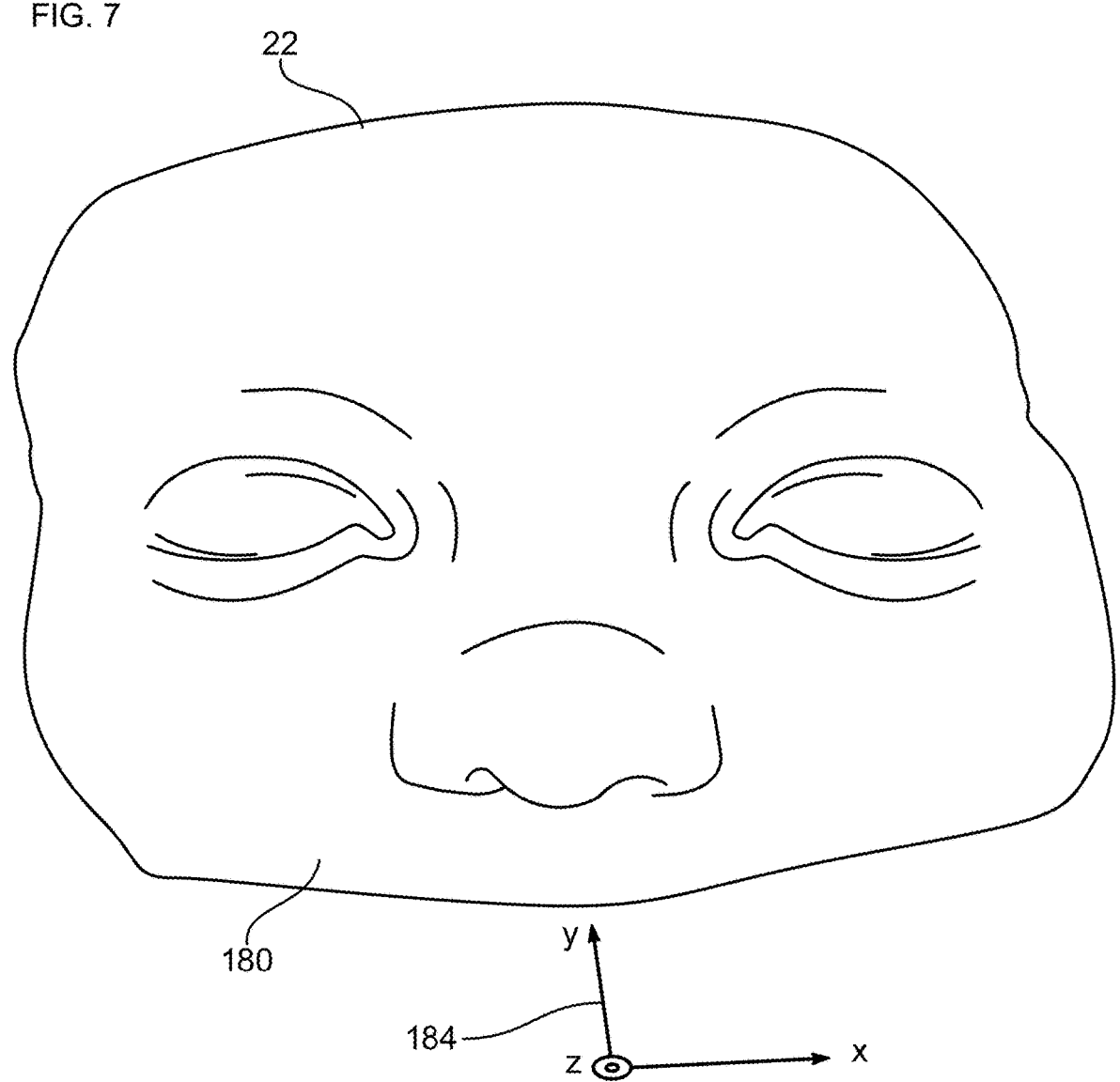

FIG. 7 is a representation of an external surface 180 of patient 22, according to an embodiment of the present invention. Processor 40 (FIG. 1) uses the CT scan data acquired in the step of block 100 to generate the representation of the external surface, by using the facts that air has a HU value of −1000 while skin has a HU value significantly different from this. By way of example, representation 180 is assumed to be formed on a plane parallel to the coronal plane of the patient 22, i.e., parallel to an x-y plane of a frame of reference 184 defined by the patient 22, the axes of which are also drawn in FIG. 7 and in FIG. 8.

Figure 8:
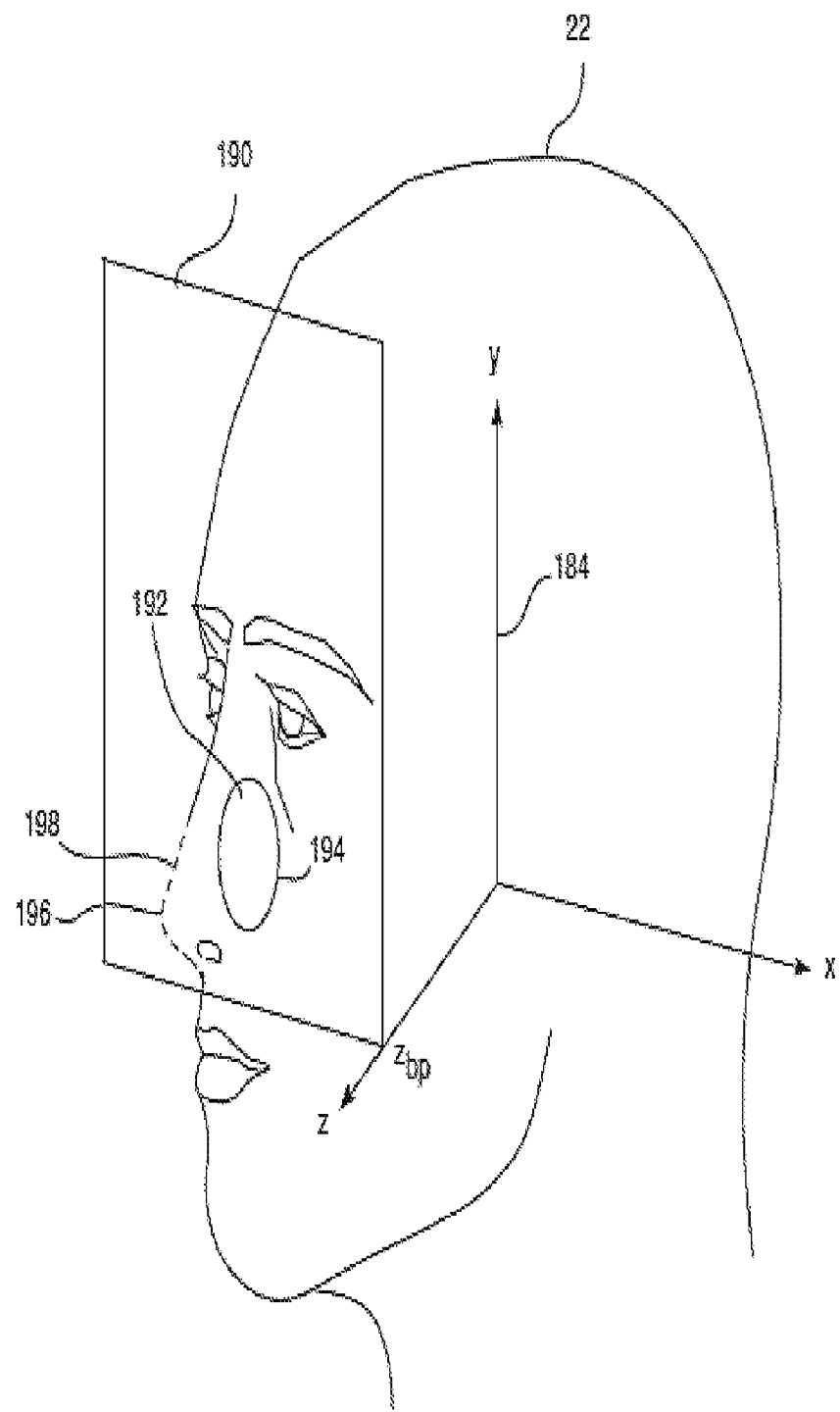

FIG. 8 schematically illustrates a boundary plane 190 and a bounding region 192, according to an embodiment of the present invention. Under directions from physician 54 (FIG. 1), processor 40 (FIG. 1) optionally delineates regions of representation 180 which are to be rendered transparent, and those which are to be left "as is." In order to perform the delineation, the physician defines boundary plane 190, and bounding region 192 in the boundary plane, using a bounding perimeter 194 for the region 192.

For clarity, the following description assumes that the boundary plane is parallel to an x-y plane of frame of reference 184, as is illustrated schematically in FIG. 8, and that it has an equation given by:

$$z = z_{bp} \quad (3)$$

As described below, processor 40 uses the boundary plane and the bounding region 192 to determine which elements of surface 180 are to be rendered locally transparent, and which elements are not to be so rendered.

Processor 40 determines elements of surface 180 (FIG. 7) having values of $z \geq z_{bp}$, and that, when projected along the z-axis, lie within bounding region 192. The processor 40 then renders the elements transparent so that, consequently, these elements are no longer visible in surface 180. For example, in FIG. 8 a tip 196 of the nose of patient 22 has a value $z \geq z_{bp}$, so a broken line 198 in the vicinity of the patient's nose tip illustrates parts of external surface 180 that are no longer visible when the image of the surface is presented on display screen 56 (FIG. 1).

In consequence of the above-defined elements being rendered transparent, elements of surface 180, having values of $z < z_{bp}$ and that when projected along the z-axis lie within bounding region 192 are now visible, so are displayed in the image. Prior to the local transparent rendering, the "now visible" elements were not visible since they were obscured by surface elements. The now visible elements include elements of shortest path 154, as is illustrated in FIG. 9.

Figure 9:
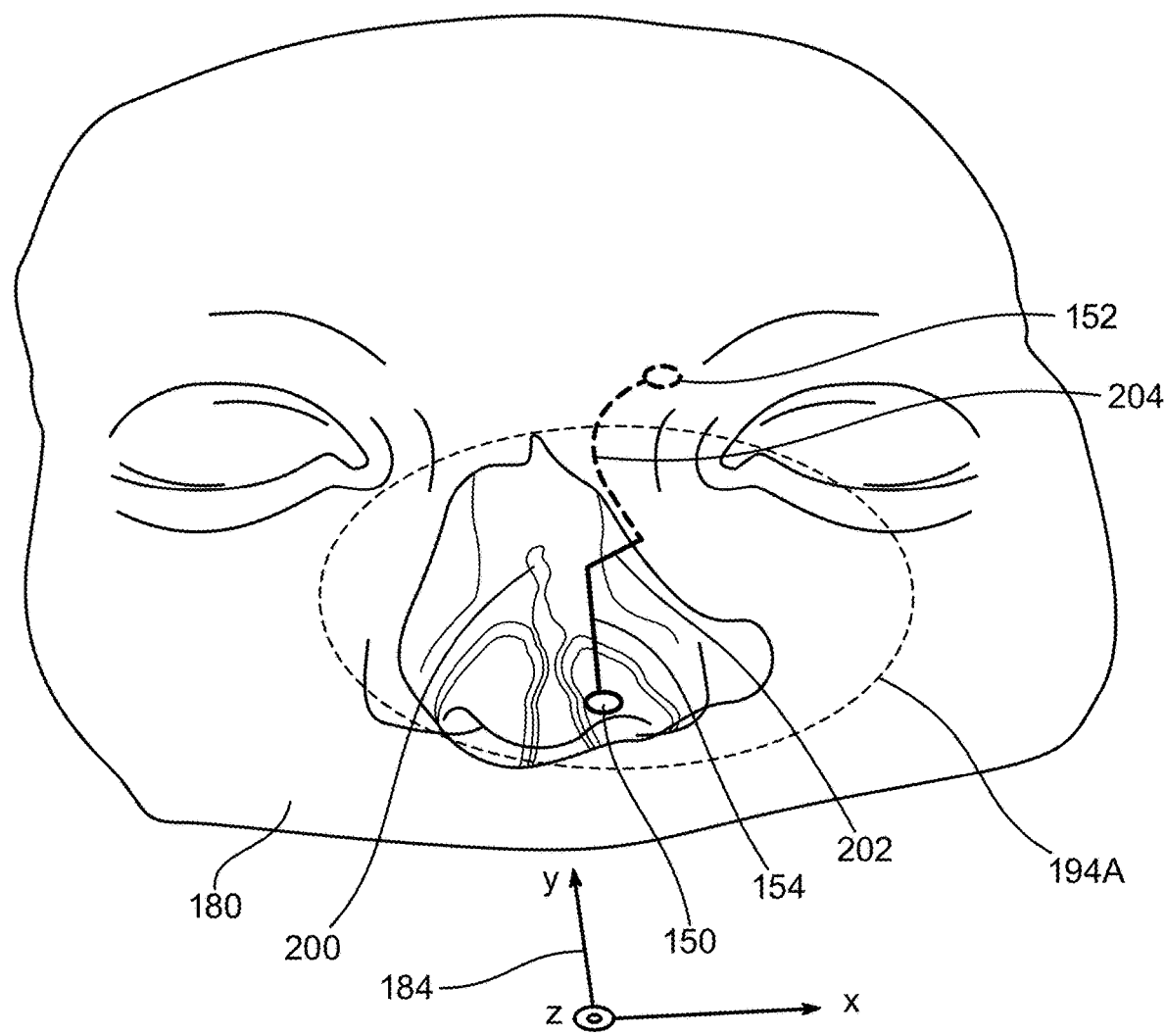

FIG. 9 schematically illustrates surface 180 as displayed on display screen 56 (FIG. 1) after the local transparency rendering of the elements of the surface within bounding region 192 (FIG. 8). For clarity a broken circle 194A, corresponding to bounding perimeter 194 (FIG. 8) has been overlaid on the image, and frame of reference 184 is also drawn in the figure. Because of the transparent rendering of elements within circle 194A, an area 200 within the circle now shows internal structure, derived from the CT tomographic data received in the step of block 100, of patient 22 (FIG. 1).

Shortest path 154 has also been drawn in FIG. 9. Because of the transparent rendering of elements within circle 194A, a portion of the path is now visible in the image of surface 180, and has been drawn as a solid while line 202. The portion of the path that is invisible, because it is hidden by elements of surface 180 that have not been rendered transparent, is shown as broken white line 204.

It will be appreciated that in the case illustrated in FIGS. 7 and 9, the image shown on the display screen 56 is a view of the patient 22 as viewed along the z axis of the x-y plane.

The description above provides one example of the application of local transparency to viewing a shortest path derived from tomographic data, the local transparency in this case being formed relative to a plane parallel to the coronal plane of the patient 22. It will be understood that because of the three-dimensional nature of the tomographic data, the data may be manipulated so that embodiments of the present invention may view the shortest path 154 using local transparency formed relative to substantially any plane through patient 22, and that may be defined in frame of reference 184.

In forming the local transparency, the dimensions and position of the boundary plane 190 and the bounding region 192 may be varied to enable the physician 54 (FIG. 1) to also view the shortest path 154, and internal structures in the vicinity of the path 154.

The physician 54 may vary the direction of the bounding plane 190, for example to enhance the visibility of particular internal structures. While the bounding plane 190 is typically parallel to the plane of the image presented on display screen 56, this is not a requirement, so that if, for example, the physician 54 wants to see more detail of a particular structure, she/he may rotate the bounding plane 190 so that it is no longer parallel to the image plane.

In some cases, the range of HU values/gray scales selected in the step of block 106 includes regions other than air, for example, regions that correspond to soft tissue and/or mucous. The path 154 found in the step of block 108 may include such regions, and in this case, for medical instrument 21 (FIG. 1) to follow the path 154, these regions may have to be cleared, for example by debriding. In an optional warning step (block 112), the physician 54 (FIG. 1) is advised of the existence of regions of path 154 that are not in air, for example by highlighting a relevant section of the path 154, and/or by other visual or auditory cues.

While the description above has assumed that the CT scan is an X-ray scan, it will be understood that embodiments of the present invention comprise finding a shortest path using MRI (magnetic resonance imaging) tomography images.

Thus, referring back to the flowchart 90, in the case of MRI images, wherein Hounsfield values may not be directly applicable, in step 106 the physician 54 (FIG. 1) defines ranges of gray scale values (of the MRI images) which the path finding algorithm uses as acceptable voxel values in finding a path from the start point 150 to the termination point 152. In the step of block 108, the path finding algorithm assumes that traversable voxels in the path include any voxels having gray scales in the gray scale range defined in the step of block 106, and that voxels having gray scale values outside this defined range act as barriers in any path found. Other changes to the description above, to accommodate using MRI images rather than X-ray CT images, will be apparent to those having ordinary skill in the art, and all such changes are to be considered as comprised within the scope of the present invention.

Figure 10:
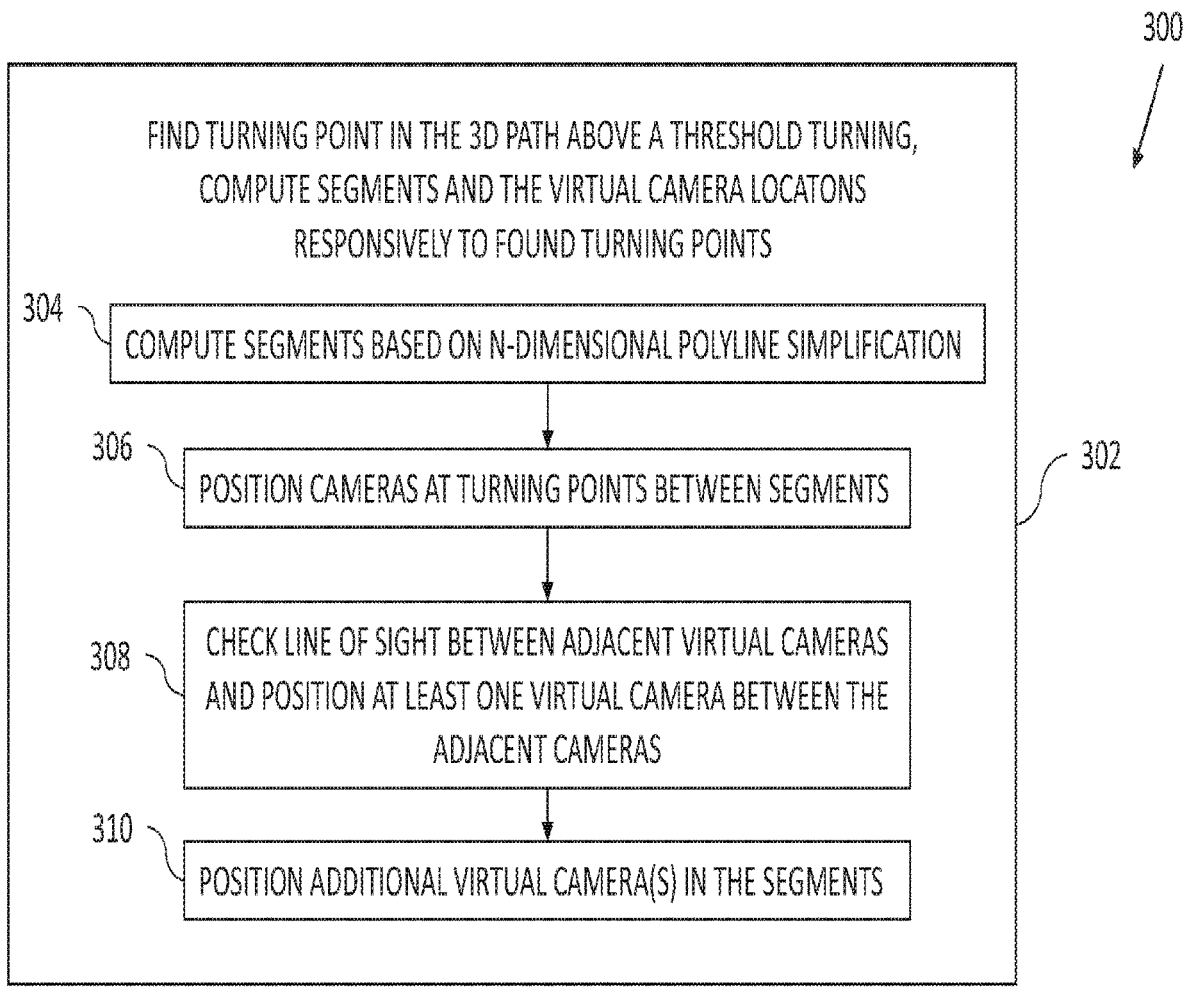
FIG. 10 is a flowchart including steps in a method of computing segments of a path and computing locations of virtual cameras along the path for use in the apparatus of FIG. 1.
Figure 11:
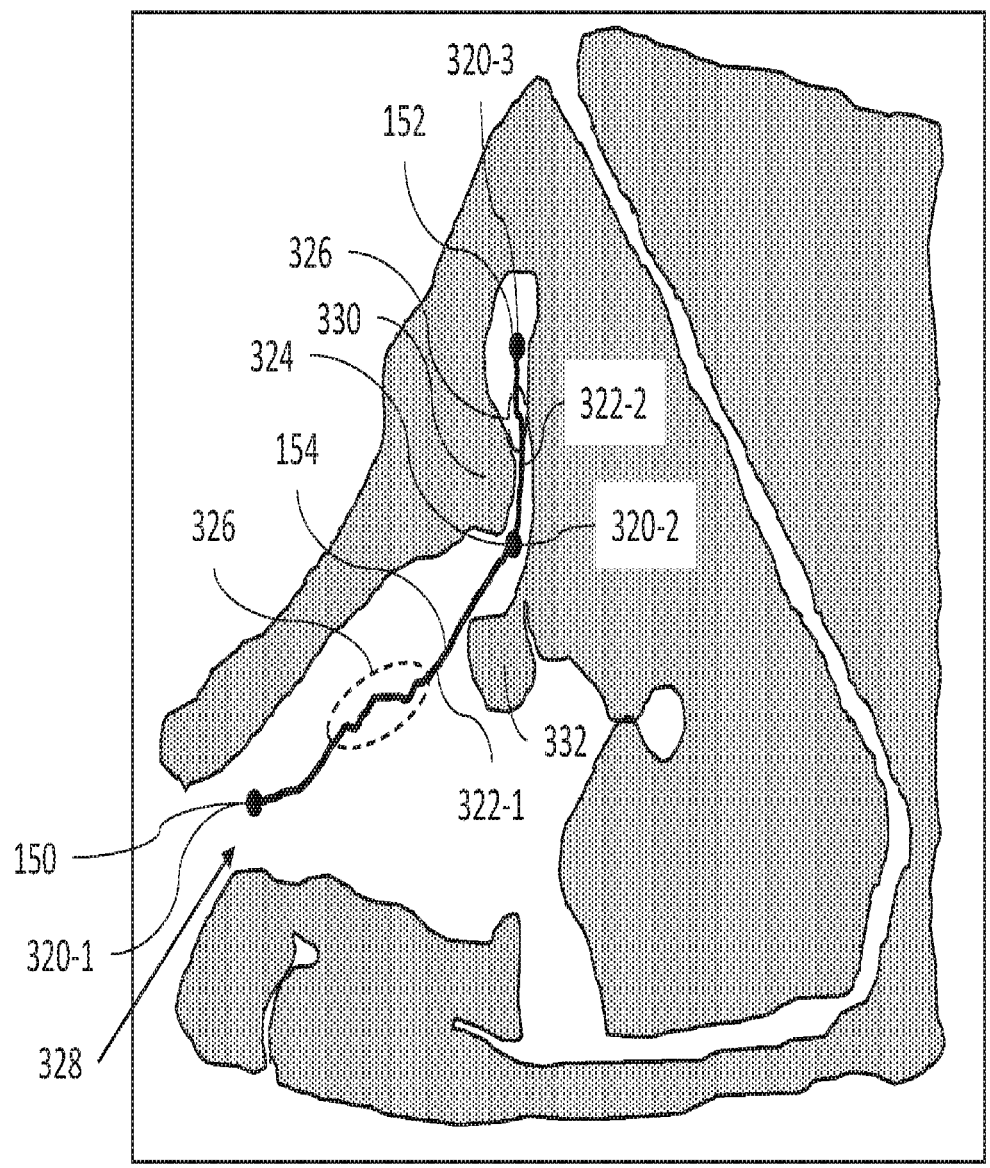
FIGS. 11 and 12 are schematic diagrams illustrating the steps of the method of the flowchart of FIG. 10.
Figure 12:
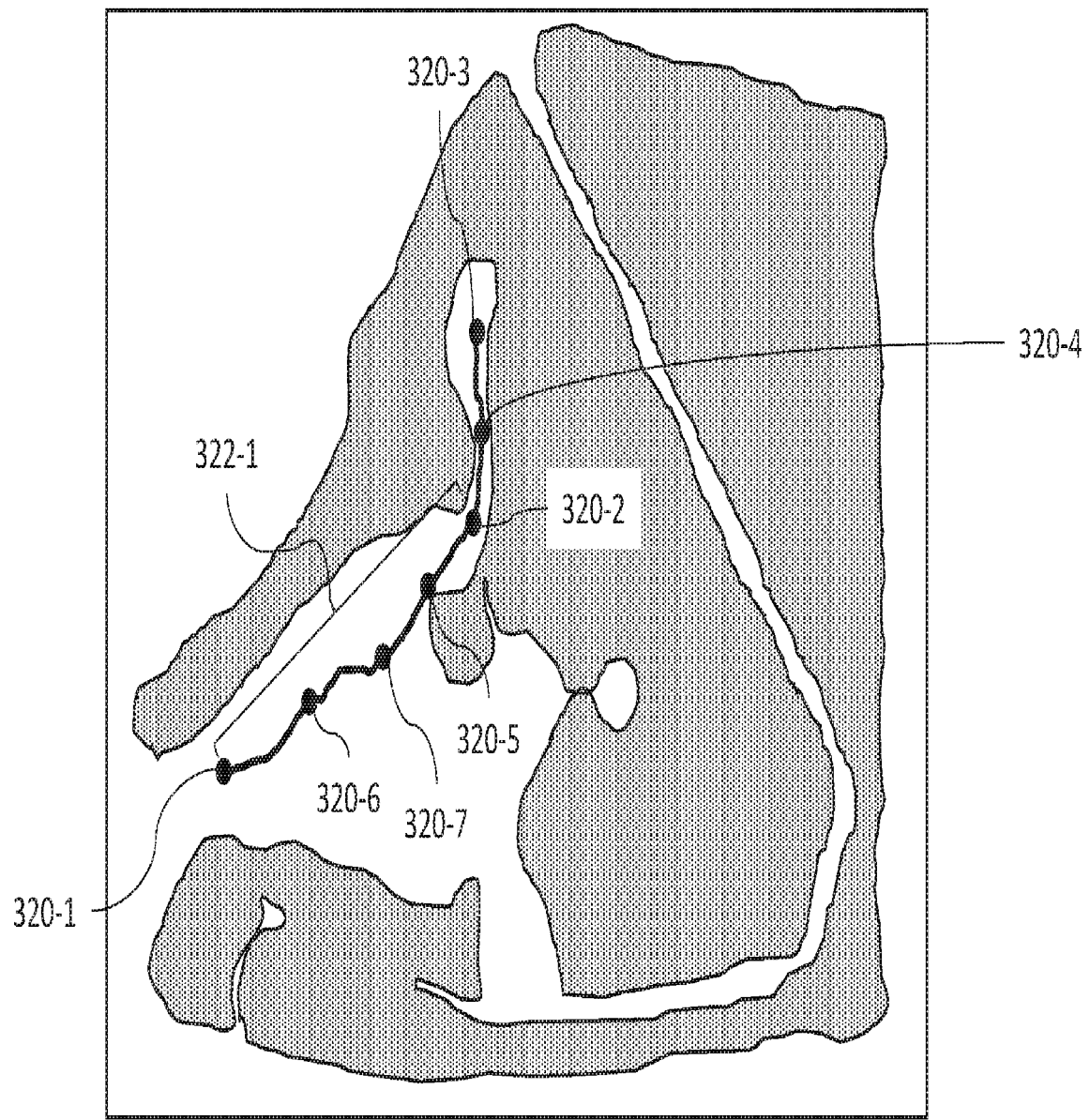

Reference is now made to FIGS. 10-12. FIG. 10 is a flowchart 300 including steps in a method of computing segments of the path 154 and computing locations of virtual cameras 320 along the path 154 for use in the apparatus 20 of FIG. 1. FIGS. 11 and 12, are schematic diagrams illustrating the steps of the method of the flowchart 300 of FIG. 10.

The processor 40 (FIG. 1) is configured to find (block 302) turning points 324 in the 3D path 154 above a threshold turning, and compute segments 322 of the 3D path 154 and respective different locations along the 3D path 154 of the respective virtual cameras 320 responsively to the found turning points 324 as shown in FIG. 11.

Sub-steps of the step of block 302 are now described below.

The processor 40 (FIG. 1) is configured to compute (block 304) the segments 322 based on an n-dimensional polyline simplification. In some embodiments, the n-dimensional polyline simplification includes the Ramer-Douglas-Peucker algorithm, the Visvalingam-Whyatt algorithm, or the Reumann-Witkam, by way of example. Any suitable algorithm which simplifies a n-dimensional polyline to a polyline of less dimensions may be used. The algorithms typically analyze the path 154 removing small turning points while leaving larger turning points so that the larger turning points 324 define segments 322 between the turning points 324. The threshold turning values corresponding to turning points which are removed from the path 154 may be set by configuring the parameters of the algorithm being used. For example, the input parameter of the Ramer-Douglas-Peucker algorithm may be set to about 0.08.

In other embodiments, the processor 40 is configured to compute the segments 322 using any suitable algorithm so that the turning points below the threshold turning value are removed.

The processor 40 (FIG. 1) is configured to position (block 306) the virtual cameras 320 at, or around, the turning points 324 between the segments 322 as well as at the start point 150 and optionally at the termination point 152 of path 154. FIG. 11 shows that the path 154 in a passage 328 has been simplified with one turning point 324 and two segments 322. Three virtual cameras 320 have been respectively placed at the start point 150, the turning point 324, and the termination point 152 on the path 154. Small turning points (indicated using a dotted line oval shape 326) on the path 154 are removed by the n-dimensional polyline simplification to leave the turning point 324.

The processor 40 is configured to check (block 308) a line of sight between two adjacent virtual cameras 320 and position one or more virtual cameras 320 between the two adjacent virtual cameras 320 responsively to the line of sight being blocked. The line of sight may be checked by examining voxels of the 3D CT image to determine if there is material blocking the line of sight between the adjacent virtual cameras 320. The type of material which is considered to block or allow the line of sight may be the same as used when computing the path 154 as described with reference to the step of block 106 of FIG. 3. In some embodiments different criteria may be used. For example, the physician 54 may set the material that blocks the line of sight as bone and hard tissue, thereby defining air, liquid and soft tissue as materials which do not block line of sight. In some cases, the physician 54 may set the material that blocks the line of sight as bone, hard tissue, and soft tissue. Alternatively, the physician 54 may set the materials that do not block the line of sight such as air or liquid, instead of specifying the materials that block the line of sight. In some embodiments, the processor 40 is configured to check that a direct line of sight between two adjacent virtual cameras 320 is not blocked. In other embodiments, the processor 40 may be configured to check that the direct line of sight between the two adjacent virtual cameras 320 is not blocked including checking that a given tolerance around the line of sight between the two virtual cameras 320 is not blocked. The given tolerance around the line of sight may have any suitable value. For example, FIG. 11 shows that the line of sight between virtual camera 320-2 and virtual camera 320-3 along the segment 322-2 is blocked by a portion of tissue 330. FIG. 12 shows that another virtual camera 320-4 has been added between virtual cameras 320-2 and 320-3. FIG. 11 also shows that although the direct line of sight between virtual cameras 320-1 and 320-2 is not blocked, when taking into account a given tolerance around the line of sight, the line of sight expanded by the given tolerance is blocked by a portion of tissue 332. FIG. 12 shows that another virtual camera 320-5 has been added between virtual cameras 320-1 and 320-2. Once the additional virtual cameras 320 have been added the processor 40 may check the line of sight (or the expanded line of sight) between the adjacent virtual cameras 320 based on the initial virtual cameras 320 plus the additional virtual cameras 320.

The processor 40 is optionally configured to position (block 310) one or more additional virtual cameras 320 in the middle of one or more of the segments 322 responsively to a distance between the existing virtual cameras 320 exceeding a limit.

FIG. 12 shows that virtual cameras 320-6 and 320-7 have been added in the segment 322-1 responsively to a distance between the existing virtual cameras 320 exceeding a limit. The limit may be any suitable limit, for example, but not limited to, in a range of 1 mm to 20 mm, such as 4 mm. The additional cameras 320 are typically spaced evenly between the existing virtual cameras 320.

Figure 13:
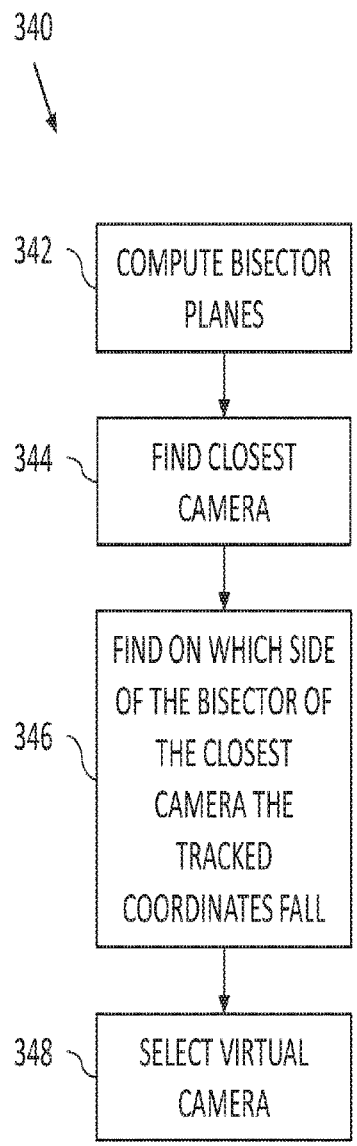
FIG. 13 is a flowchart including steps in a method of selecting a camera for use in the apparatus of FIG. 1.
Figure 14:
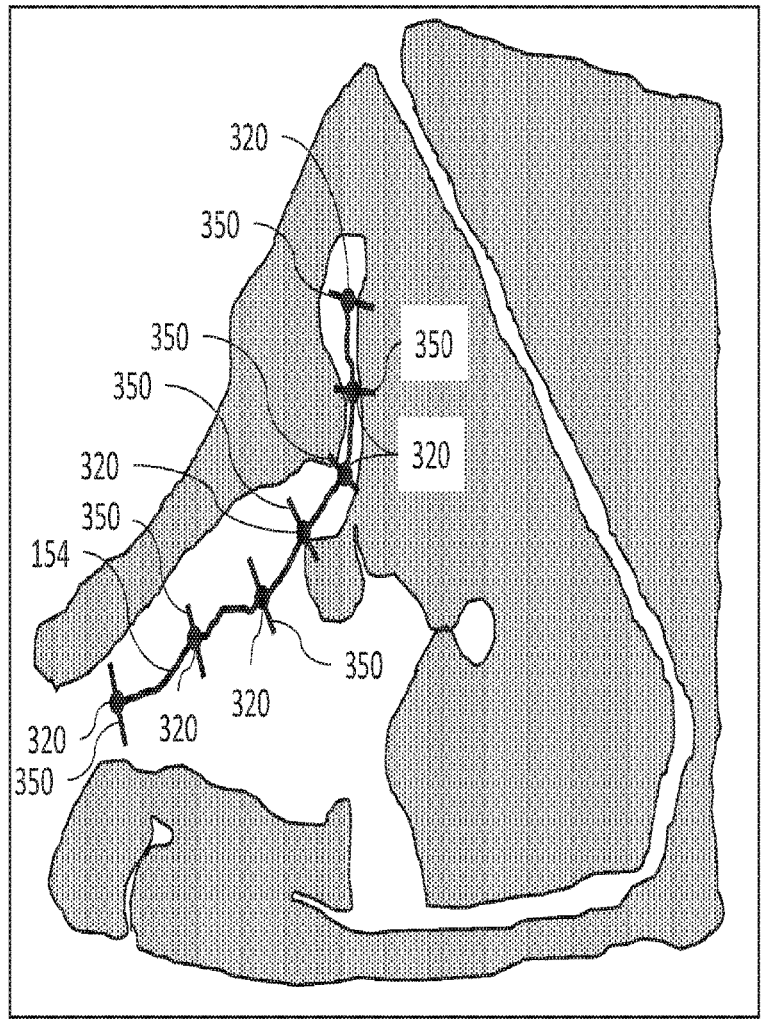
FIGS. 14 and 15 are schematic diagrams illustrating the steps of the method of the flowchart of FIG. 13.
Figure 15:
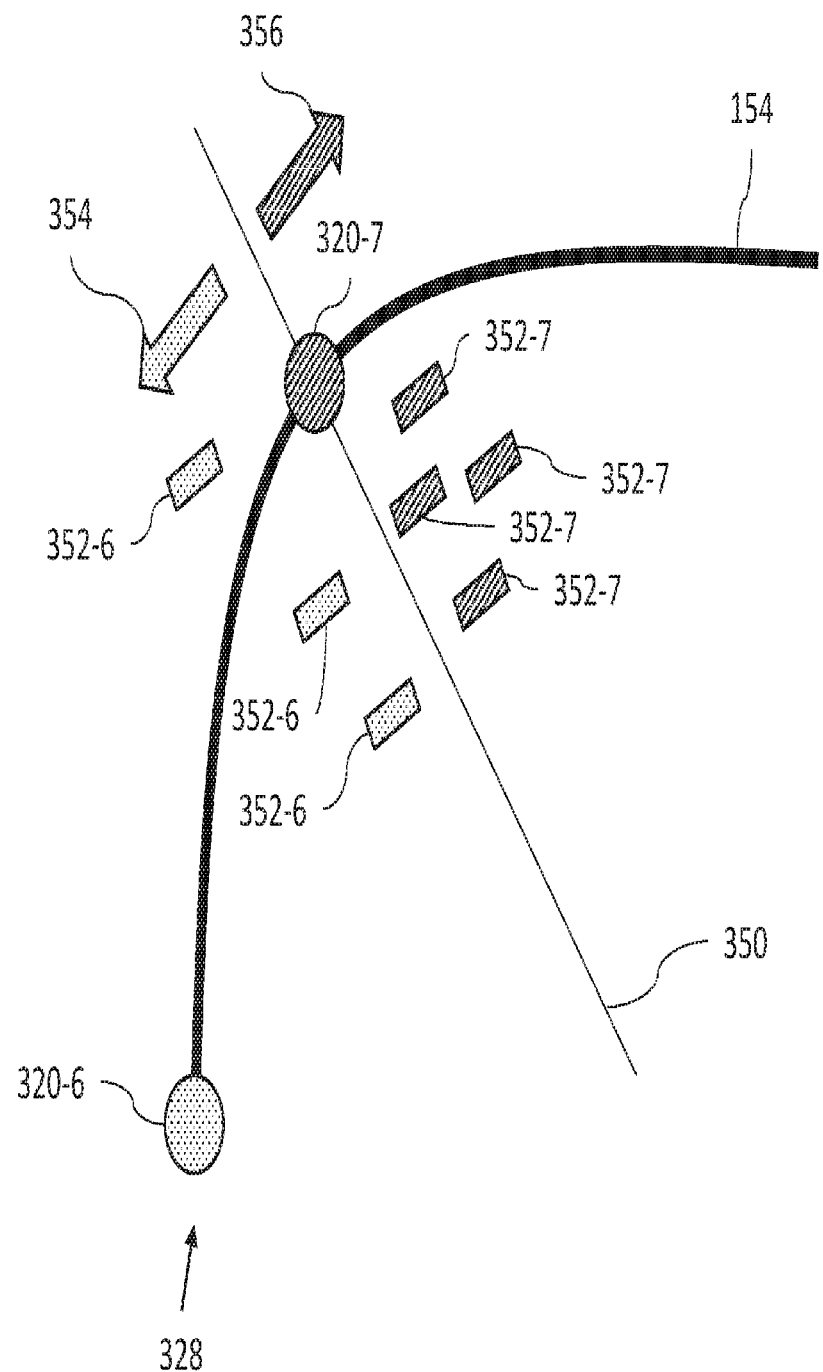

Reference is now made to FIGS. 13-15. FIG. 13 is a flowchart 340 including steps in a method of selecting a camera for use in the apparatus 20 of FIG. 1. FIGS. 14 and 15 are schematic diagrams illustrating the steps of the method of the flowchart 340 of FIG. 13.

The processor 40 (FIG. 1) is configured to compute (block 342) respective bisectors 350 (FIG. 14) for respective ones of the virtual cameras 320. In some embodiments, the processor 40 is configured to compute the respective bisectors 350 as respective planes perpendicular to the 3D path 154 at respective locations of the respective virtual cameras 320 on the 3D path 154. FIG. 14 shows the bisectors 350 for each of the virtual cameras 320. The bisectors 350 may be computed any time after the path 154 has been computed up until the time when the medical instrument 21 is in close proximity to the respective virtual camera 320 as described in the step of block 344 below.

The processor 40 is configured to find (block 344) the closest virtual camera 320 (e.g., virtual camera 320-7) to the distal end of the medical instrument 21 (FIG. 1) responsively to the tracked coordinates of the medical instrument 21 and the known locations of the virtual cameras 320. The processor 40 is configured to find (block 346) on which side of the bisector 350 of the closest virtual camera 320 (e.g., virtual camera 320-7) the tracked coordinates fall. The processor 40 is configured to select (block 348) one of the virtual cameras 320 to use for rendering the virtual endoscopic image based on which side the tracked coordinates of the medical instrument 21 fall with respect to the bisector 350 of the closest virtual camera 320 (e.g., virtual camera 320-7). If the tracked coordinates fall on the side of the bisector 350 closer to the current virtual camera 320 (e.g., virtual camera 320-6), the current virtual camera (e.g., virtual camera 320-6) is still used. If the tracked coordinates fall on the side of the bisector 350 further away from the current virtual camera 320 (e.g., virtual camera 320-6), the next virtual camera 320 (i.e. the closest virtual camera 320 (e.g., virtual camera 320-7)) along the path is selected as the new virtual camera 320. The steps of blocks 344-346 are repeated intermittently.

The steps of blocks 344-348 are illustrated in FIG. 15. FIG. 15 shows two virtual cameras 320-6 and 320-7. The virtual camera 320-6 is the current virtual camera being used to render and display the virtual endoscopic image of the passage 328. The virtual camera 320-7 is further down the path 154 with respect to the direction of travel of the medical instrument 21 than virtual camera 320-6. In other words, virtual camera 320-7 is closer to the termination point 152 (FIG. 11) than virtual camera 320-6. FIG. 15 shows various possible example positions 352 of the distal end of medical instrument 21. All the positions 352 are closer to the virtual camera 320-7 than to the virtual camera 320-6. Therefore, for all the positions 352 shown in FIG. 15, the virtual camera 320-7 will be found to be the closest virtual camera 320 in the step of block 344. Once the closest virtual camera 320-7 is found, the position of the distal end of the medical instrument 21 with respect to the bisector 350 of the closest virtual camera 320-7 is examined in the step of block 346. In the example of FIG. 15, the positions 352-6 are located on the side (indicated by arrow 354) of the bisector 350 closest to the virtual camera 320-6 (the current virtual camera) and the positions 352-7 are on the other side (indicated by arrow 356) of the bisector 350 further away from the current virtual camera 320-6. In the example of FIG. 15, according to the step of block 348, if the tracked coordinates of the distal end of the medical instrument 21 are at any of the positions 352-6 or similar positions, the current virtual camera 320-6 will remain as the selected virtual camera. If the tracked coordinates of the distal end of the medical instrument 21 are at any of the positions 352-7 or similar positions, the virtual camera 320-7 will be selected as the new virtual camera.

Therefore, the processor 40 is configured to select the respective virtual cameras 320 for rendering respective virtual endoscopic images responsively to which side the tracked coordinates (positions 352) of the medical instrument 21 (FIG. 1) fall with respect to respective bisectors 350 of respective virtual cameras 320 closest to the tracked coordinates.

In other embodiments, the passages may be divided into regions based on the segments 322 with the virtual cameras 320 being selected according to the region in which the tracked coordinates are disposed.

Figure 16:
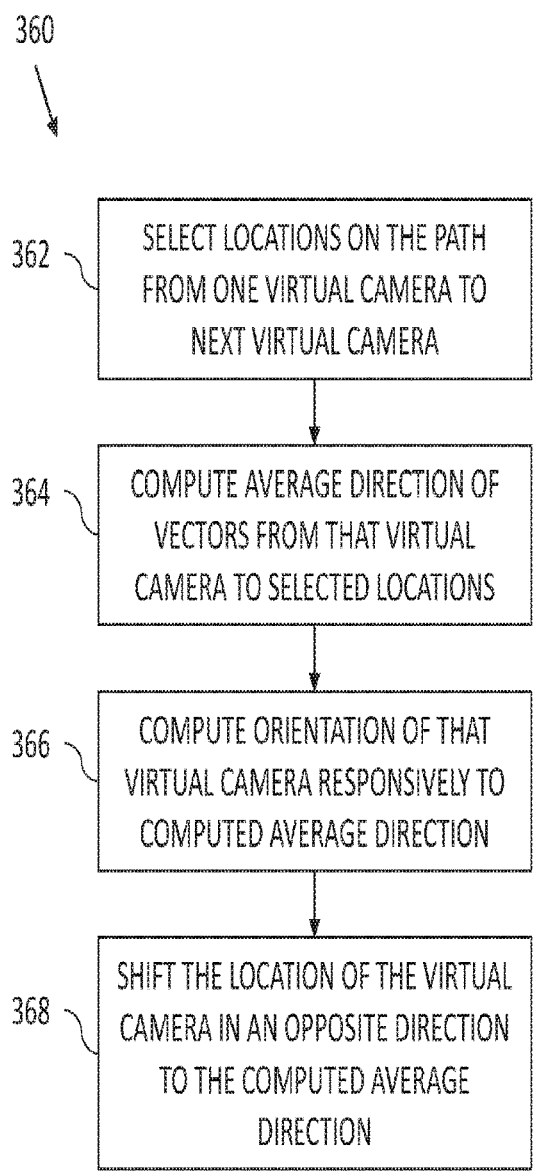
FIG. 16 is a flowchart including steps in a method of computing an orientation and shifting the location of a virtual camera for use in the apparatus of FIG. 1.
Figure 17:
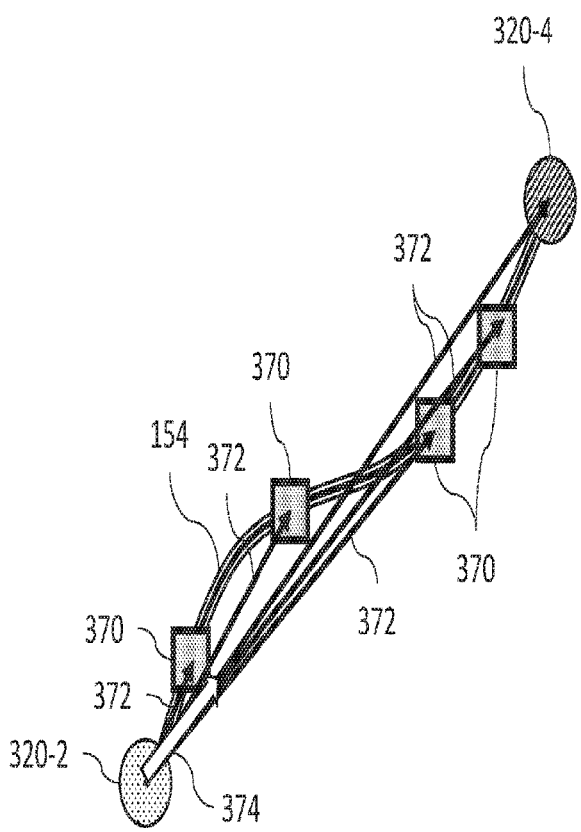
FIGS. 17 and 18 are schematic diagrams illustrating the steps of the method of the flowchart of FIG. 16.
Figure 18:
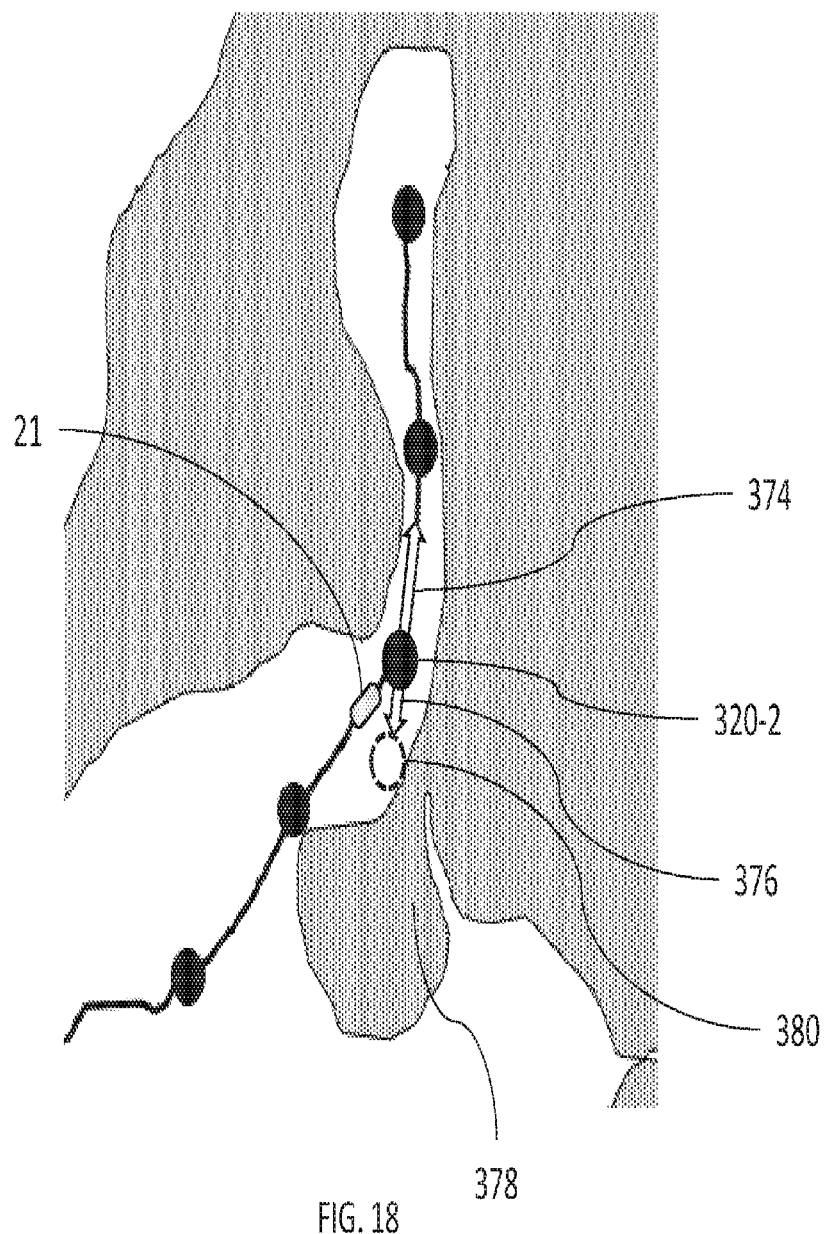

Reference is now made to FIG. 16, which is a flowchart 360 including steps in a method of computing an orientation and shifting the location of one virtual camera 320 for use in the apparatus 20 of FIG. 1. Reference is also made to FIGS. 17 and 18, which are schematic diagrams illustrating the steps of the method of the flowchart 360 of FIG. 16.

The orientation of the optical axis of each virtual camera 320 is computed. The orientation may be computed any time after the locations of the virtual cameras 320 have been computed. In some embodiments, the orientations of the virtual cameras 320 may be computed as each virtual camera 320 is selected for use as the medical instrument 21 (FIG. 1) is being moved along the path 154. One method to computed the orientation of one virtual camera 320 is now described below.

The processor 40 (FIG. 1) is configured to select (block 362) locations 370 on the path 154 from one virtual camera 320-2 to another virtual camera 320-4 as shown in FIG. 17. The locations 370 may be selected to be inclusive or exclusive of the location of the virtual camera 320-4. The locations 370 may be selected by dividing the segment 322 between the virtual cameras 320-2 and 320-4 into subsegments. Alternatively, the locations 370 may be selected by measuring a given distance along the path 154 from the virtual camera 320-2 to each location 370. In some embodiments, the locations 370 may be selected using points that define the path 154 when the path 154 was generated. The processor 40 (FIG. 1) is configured to define vectors 372 from the virtual camera 320-2 to the locations 370 and compute (block 364) an average direction 374 of the vectors 372 as shown in FIG. 17. Therefore, the processor 40 is configured to compute an average direction of the vectors from the location of the virtual camera 320-2 to different points (e.g., the locations 370) along the 3D path 154. The processor 40 (FIG. 1) is configured to compute (block 366) the orientation of the virtual camera 320-2 responsively to the computed average direction 374. In other words, the orientation of the optical axis of the virtual cameras 320 is computed as the average direction 374. In other embodiments, the orientation may be computed as a direction parallel to the path at the location of the respective virtual camera 320-2.

In some embodiments, the respective locations of the respective virtual cameras 320 (e.g., virtual camera 320-2) may be shifted back, for example, in an opposite direction 376 to the respective average directions 374 of the respective virtual cameras 320 as shown in FIG. 18. Shifting the virtual cameras 320 back may result in a better view of the medical instrument 21 within the respective virtual endoscopic images particularly when the medical instrument 21 is very close to the respective virtual cameras 320, and may result in a better view of the surrounding anatomy. Therefore, the processor 40 (FIG. 1) is configured to shift (block 368) the location of the virtual camera 320-2 in the opposite direction 376 to the computed average direction 374 to a new location 380 as shown in FIG. 18. The extent of the shift may be fixed, e.g., a predetermined number of millimeters, such as in a range between 0.2 and 2 mm, e.g. 1.3 mm. Alternatively, the extent of the shift may be limited by a surrounding anatomy 378 so that the camera 320-2 is shifted back as much as possible as long as it is not pushed into bone or tissue, as defined by the physician 54. The type of material considered "surrounding anatomy" may be the same or different criteria as used to define the material which blocks a path of the medical instrument 21 as described with reference to the step of block 106 of FIG. 3.

The field of view of the respective virtual cameras 320 may be set to any suitable respective values. The field of view of each virtual camera 320 may be fixed, for example, in a range of values between 25-170 degrees, e.g., 90 degrees. The field of view of any one virtual camera 320 may be set according to the outer limits of the segment 322 of the path 254 that that virtual camera 320 covers (for example, derived from the vectors 372 of FIG. 17 or by finding the outer limits of the segments 322) with an additional tolerance (such as a given angular tolerance for example, by adding X degrees on to the outer limits, where X may be any suitable value, for example, in a range between 5 and 90 degrees) for that virtual camera 320. In some embodiments, the field of view may be set to encompass all the anatomy in the segment 322 until the next virtual camera by analyzing the surrounding anatomy 378 around the segment 322. The type of material considered "surrounding anatomy" may be the same or different criteria as used to define the material which blocks a path of the medical instrument 21 as described with reference to the step of block 106 of FIG. 3.

Figure 19:
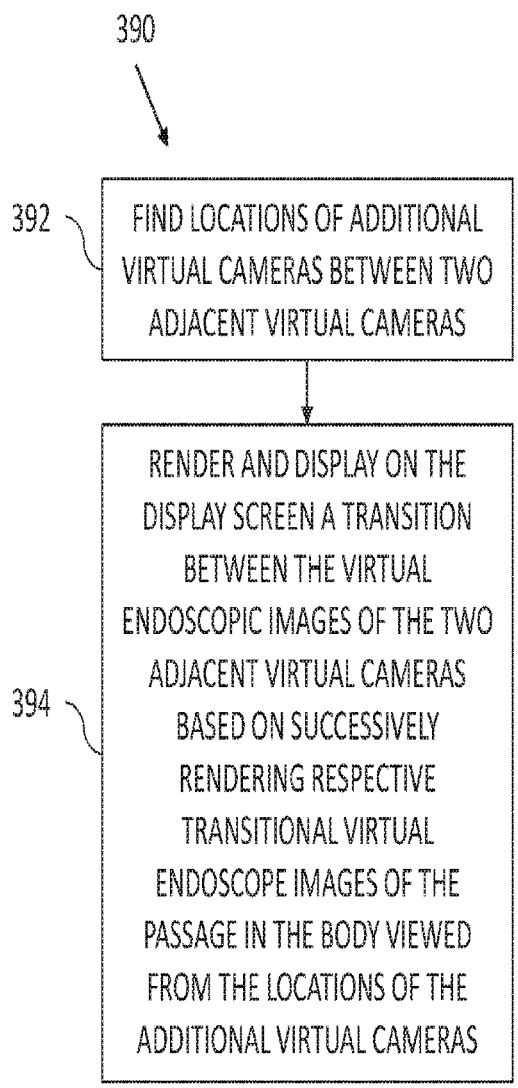
FIG. 19 is a flowchart including steps in a method of rendering a transition for use in the apparatus of FIG. 1.
Figure 20:
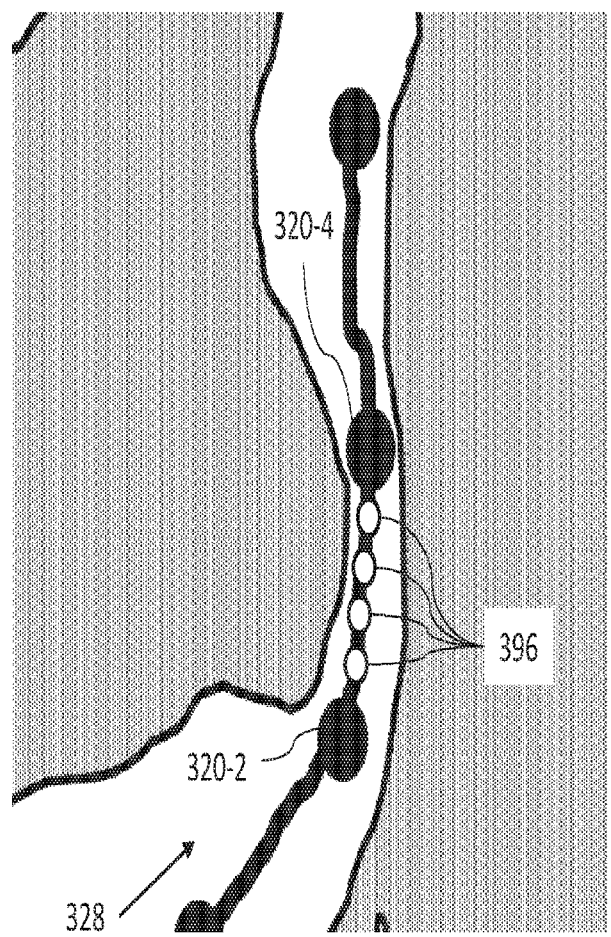
FIG. 20 is a schematic diagram illustrating the steps of the method of the flowchart of FIG. 19.

Reference is now made to FIG. 19, which is a flowchart 390 including steps in a method of rendering a transition for use in the apparatus 20 of FIG. 1. Reference is also made to FIG. 20, which is a schematic diagram illustrating the steps of the method of the flowchart 390 of FIG. 19.

The transition between two virtual cameras 320 and therefore the transition between the associated virtual endoscopic images may be a smooth transition or a sharp transition. In some embodiments, a smooth transition between the two respective virtual cameras may be performed by performing the following steps. The transition is described by way of example between virtual camera 320-2 and virtual camera 320-4.

The processor 40 (FIG. 1) is configured to find (block 392) locations of additional virtual cameras 396 to be added between the current virtual camera 320-2 and the next virtual camera 320-4 as shown in FIG. 20. The locations of the additional virtual cameras 396 may be found in a similar manner to the selection of the locations 370 described with reference to FIGS. 16 and 17. Any suitable number of additional virtual cameras 396 may be selected. A larger number of additional virtual cameras 396 will generally lead to a smoother transition.

The processor 40 (FIG. 1) is configured to render and display (block 394) on the display screen 56 (FIG. 1) a transition between two respective virtual endoscopic images of two respective adjacent virtual cameras 320-2, 320-4 based on successively rendering respective transitional virtual endoscope images of the passage 328 (FIG. 20) in the body viewed from respective locations of respective additional virtual cameras 396 disposed between the two adjacent virtual cameras 320-2, 320-4. Each of the transitional virtual endoscope images may be displayed on the display screen 56 for any suitable duration, for example, a duration in the range of 20 to 40 milliseconds.

Figure 21:
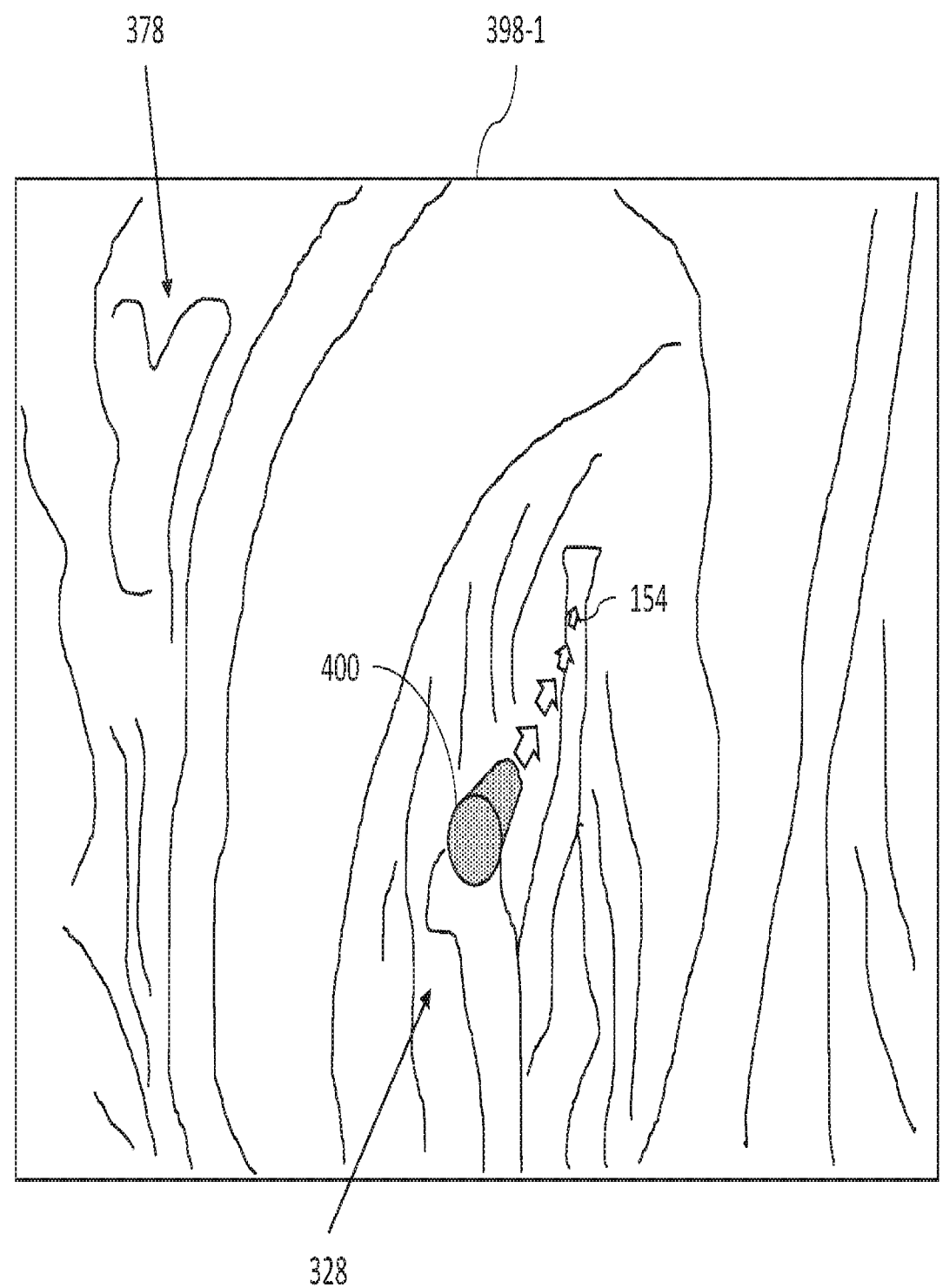
FIGS. 21-23 are schematic virtual endoscopic images rendered and displayed by the apparatus of FIG. 1.
Figure 22:
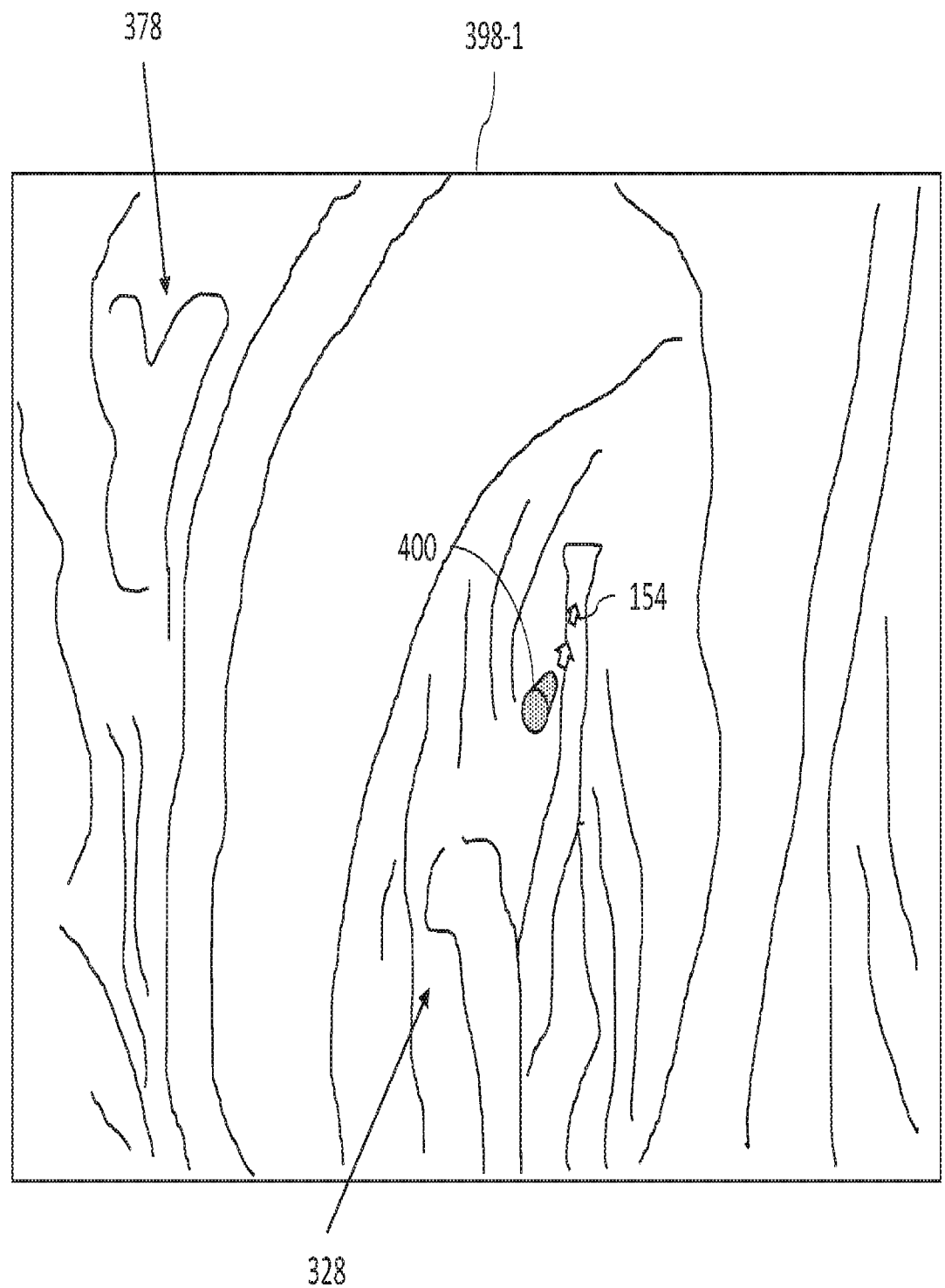
Figure 23:
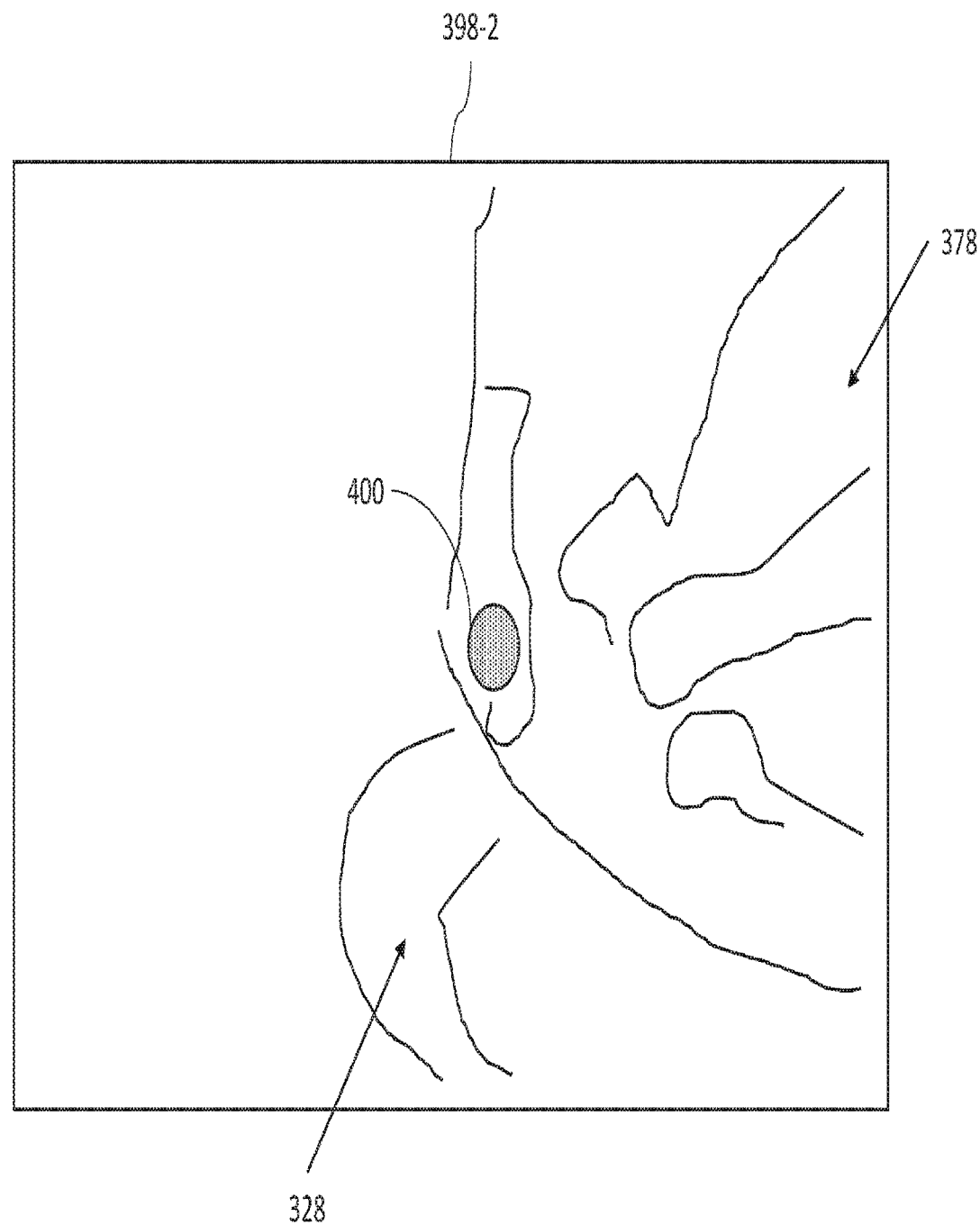

Reference is now made to FIGS. 21-23, which are schematic virtual endoscopic images 398 rendered and displayed by the apparatus 20 of FIG. 1. As previously mentioned with reference to FIG. 2, the processor 40 (FIG. 1) is configured to render and display on the display screen 56 (FIG. 1) the respective virtual endoscopic images 398, based on the 3D CT image, of the passage 328 in the body viewed from the respective locations and orientations of the respective virtual cameras 320 (FIG. 11) including an animated representation 400 of the medical instrument 21 (FIG. 1) positioned in the respective virtual endoscopic images 398 in accordance with the tracked coordinates of the medical instrument 21.

FIGS. 21-22 show the virtual endoscopic image 398-1 viewed from the location of one virtual camera 320. The representation 400 of the medical instrument 21 is shown in FIG. 21 at one position in the passage 328 along the path 154 and in FIG. 22 at a more advanced position in the passage 328 along the path 154. The path 154 which still remains to be traversed is shown using arrows which disappear as the medical instrument 21 moves along the path 154. Any suitably line or symbol may be used to represent the path 154. FIG. 23 shows the virtual endoscopic image 398-2 viewed from the location of another virtual camera 320.

The virtual endoscopic images 398 may be rendered using volume visualization techniques generating the virtual endoscopic images 398 from tissue image data (e.g., based on the HU of voxels of the 3D CT scan) in a 3D viewing volume such as a cone projecting outward from the location of the relevant virtual camera 320. The images 398 may be rendered based on known colors of the tissue. Certain materials such as liquids or even soft tissue may be selected to be transparent while all other denser material may be rendered according to the natural color of the denser material. Alternatively, even liquids and soft tissue along with the denser material may be rendered according to the natural color of the respective materials. In some embodiments, the physician 54 (FIG. 1) may be set the rendering parameters of the virtual endoscopic images 398 discussed above. In some embodiments, the surrounding anatomy 378 may be rendered whereas other anatomy may be ignored. The type of material considered "surrounding anatomy" may be the same or different criteria as used to define material through which the path 154 cannot pass as described with reference to the step of block 106 of FIG. 3.

The above images 398 are presented only for purposes of illustration, and other sorts of images may likewise be rendered and displayed in accordance with the principles of the present invention.

Figure 24:
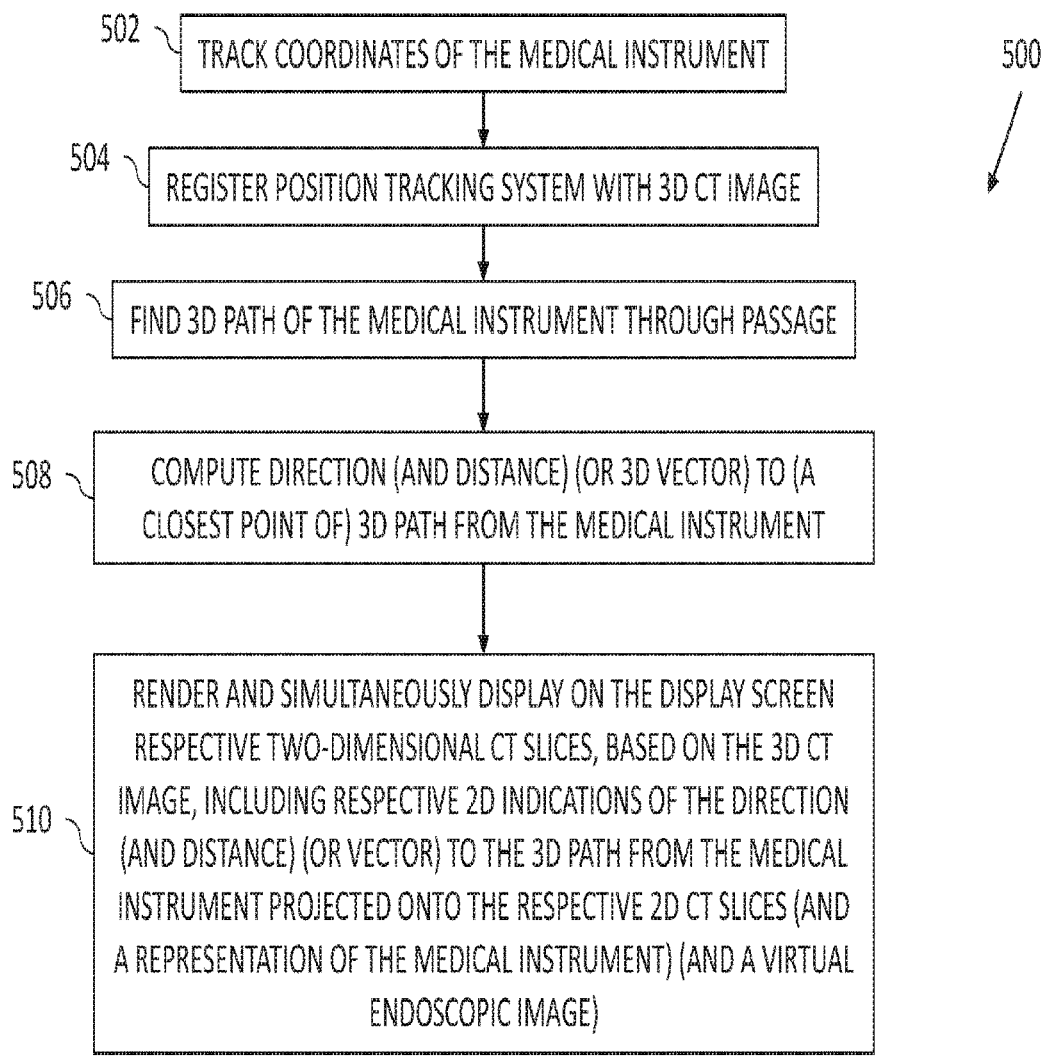
FIG. 24 is a flowchart including steps in a method of two-dimensional path visualization for use in the apparatus of FIG. 1 in accordance with an embodiment of the present invention.
Figure 25:
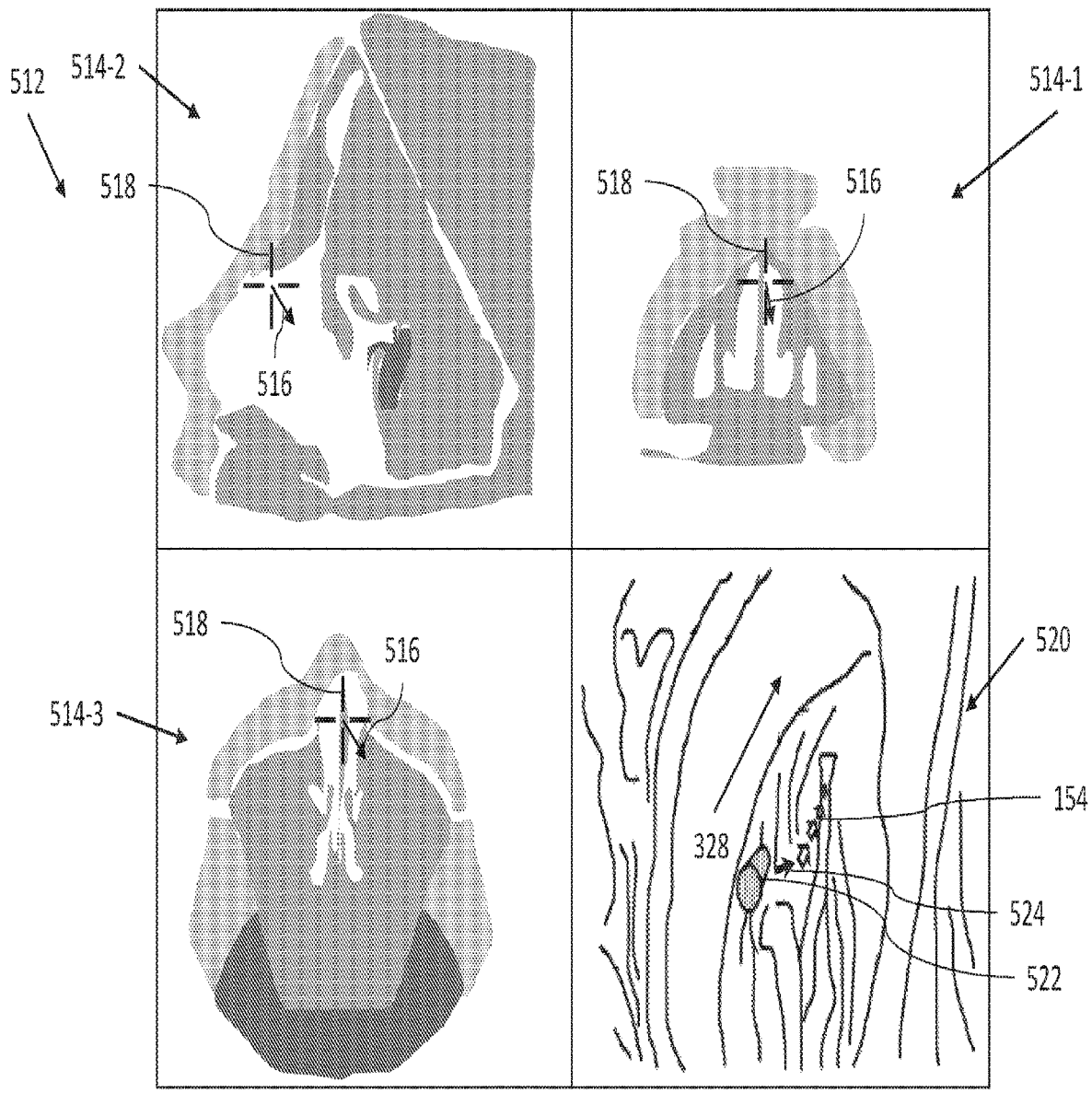
FIG. 25 is a schematic view of a combined 2D and 3D path visualization illustrating the steps of the method of the flowchart of FIG. 24.

Reference is now made to FIGS. 24 and 25. FIG. 24 is a flowchart 500 including steps in a method of two-dimensional path visualization for use in the apparatus 20 of FIG. 1 in accordance with an embodiment of the present invention. FIG. 25 is a schematic view of a combined 2D and 3D path visualization 512 illustrating the steps of the method of the flowchart 500 of FIG. 24.

The position tracking system 23 (FIG. 1) is configured to track (block 502) coordinates of the medical instrument 21 (FIG. 1) within the body. The processor 40 (FIG. 1) is configured to register (block 504) the position tracking system 23 and a three-dimensional (3D) computerized tomography (CT) image of at least a part of the body within a common frame of reference. The step of block 504 is substantially the same as the step of block 74 described in detail with reference to FIG. 2.

The processor 40 (FIG. 1) is configured to find (block 506) the 3D path 154 (FIG. 25) of the medical instrument 21 (FIG. 1) through the passage 328 (FIG. 25) passage from the given start point 150 (FIG. 9) to the given termination point 152 (FIG. 9) within the common frame of reference. The step of block 506 is substantially the same as the step of block 76 described in detail with reference to FIG. 2.

The processor 40 (FIG. 1) is configured to compute (block 508) a direction, and optionally a distance, and/or a 3D vector, to the 3D path 154 from the distal end of the medical instrument 21 (FIG. 1) responsively to the tracked coordinates of the medical instrument 21. In some embodiments, the processor 40 is configured to compute a direction, and optionally a distance, and/or a 3D vector, to a closest point of the 3D path 154 from the distal end of the medical instrument 21 responsively to the tracked coordinates of the medical instrument 21.

The processor 40 (FIG. 1) is configured to render and simultaneously display (block 510) on the display screen 56 (FIG. 1) respective two-dimensional (2D) CT slices 514, based on the 3D CT image, including respective 2D indications 516 of the direction, and optionally the distance, and/or the 3D vector, to the 3D path 154 from the distal end of the medical instrument 21 projected onto the respective 2D CT slices 514, and optionally a representation 518 of the medical instrument 21 responsively to the tracked coordinates of the medical instrument 21.

The 2D CT slices 514 are generated from the 3D CT image according to the tracked coordinates of the distal end of the medical instrument 21 such that the 2D CT slices 514 are planes that intersect in the 3D CT image at the tracked coordinates. In some embodiments, the processor 40 is configured to render and simultaneously display, on the display screen 56 (FIG. 1), three respective two-dimensional (2D) CT slices 514 including respective 2D indications 516 of the direction, and optionally the distance, and/or the 3D vector, to the (closest point of the) 3D path 154 from the distal end of the medical instrument 21 projected onto the three respective 2D CT slices 514, and optionally a representation 518 of the medical instrument 21 responsively to the tracked coordinates of the medical instrument 21. In some embodiments, the three respective 2D slices respectively include a Coronal view slice 514-1, a Sagittal view slice 514-2, and a Transversal view slice 514-3.

The 2D indications 516 may include any suitable symbol such as an arrow or pointer. The 2D indications 516 may indicate only the direction to the path 154 and therefore all the 2D indications 516 may be the same length irrespective of the distance to the path 154. In some embodiments, the 2D indications 516 may indicate the direction and distance (or the 3D vector) to the path 154 and the 2D indications 516 may be sized (length and/or width) according to the distance to the path 154. The 2D indications 516 represent the direction, and optionally distance or vector to the path projected on to the respective 2D CT slices 514. For example, based on the frame of reference 184 shown in FIG. 8, the 3D vector is projected on to the x-y plane to generate the 2D indication 516 for the Coronal view slice 514-1, on to the y-z plane to generate the 2D indication 516 for the Sagittal view slice 514-2, and on to the x-z plane to generate the 2D indication 516 for the Transversal view slice 514-3.

The representation 518 of the medical instrument 21 (FIG. 1) may include any suitable symbol, for example, a cross or a circle.

In some embodiments, the processor 40 (FIG. 1) is configured to render and simultaneously display on the display screen: (a) the respective 2D CT slices 514 including the respective 2D indications 516 of the direction to the 3D path 154 from the medical instrument 21 projected onto the respective 2D CT slices 514; and a virtual endoscopic image 520, based on the 3D CT image, of the passage 328 in the body viewed from at least one respective location of at least one respective virtual camera including an animated representation 522 of the medical instrument 21 positioned in the virtual endoscopic image 520 in accordance with the tracked coordinates, and a 3D indication 524 of the direction to the 3D path 154 from the medical instrument 21. The virtual endoscopic image 520 may be rendered and displayed according to the methods described above with reference to FIGS. 2-23.

The above images 514, 520 are presented only for purposes of illustration, and other sorts of images may likewise be rendered and displayed in accordance with the principles of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical apparatus, comprising:
    (a) a medical instrument, which is configured to move within a body of a patient;
    (b) a position tracking system, which is configured to track coordinates of the medical instrument within the body;
    (c) a display screen; and
    (d) a processor, which is configured to:
        (i) obtain, based on preoperative image data, three-dimensional (3D) data representative of at least a part of the body within a common frame of reference,
        (ii) receive a start point and a termination point associated with the body,
        (iii) calculate, based on the 3D data, a 3D path of the medical instrument from the start point to the termination point,
        (iv) identify, based on the 3D data, one or more turning points along the 3D path that exceed a curvature threshold, and
        (v) display, on the display screen, a virtual camera view for one or more of the turning points comprising a virtual representation of the medical instrument relative to two-dimensional (2D) preoperative image data, including respective 2D indications of a desired direction to the 3D path from the medical instrument.

2. The apparatus according to claim 1, wherein the preoperative image data comprises 3D voxel data.

3. The apparatus according to claim 2, wherein the calculating of the 3D path of the medical instrument through the body further comprises calculating a Hounsfield Unit (HU) value for a set of voxels from the 3D voxel data.

4. The apparatus according to claim 2, wherein the processor is further configured to identify, based on the 3D voxel data, one or more non-air sections along the 3D path, and wherein the virtual camera view further comprises at least one visual cue associated with the non-air sections.

5. The apparatus according to claim 2, wherein the virtual camera view further comprises a virtual endoscopic image, based on the 3D voxel data, viewed from at least one respective location of at least one respective virtual camera including an animated representation of the medical instrument positioned in the virtual endoscopic image in accordance with the tracked coordinates, and a 3D indication of the direction to the 3D path from the medical instrument.

6. The apparatus according to claim 1, wherein the processor is configured to identify a point along the 3D path that is closest to the tracked coordinates of the medical instrument, and compute a 3D vector relative to the point and the tracked coordinates of the medical instrument, and wherein the 2D indications are based on the 3D vector.

7. The Apparatus according to claim 1, wherein the processor is further configured to provide for user selection a virtual camera view for each of the one or more turning points via the display screen, and wherein the virtual camera view displayed on the display is based on the user selection.

8. The apparatus according to claim 1, wherein the virtual camera view further comprises three respective 2D CT slices including three respective 2D indications of the direction.

9. The apparatus according to claim 8, wherein the three respective 2D slices respectively include a Coronal view, a Sagittal view, and a Transversal view.

10. The apparatus according to claim 1, wherein the position tracking system comprises an electromagnetic tracking system, which comprises one or more magnetic field generators positioned around the part of the body and a magnetic field sensor at a distal end of the medical instrument.

11. The apparatus according to claim 1, wherein the respective 2D indications of the desired direction to the 3D path from the medical instrument include respective arrows.

12. A medical method, comprising:
    (a) tracking coordinates of a medical instrument within a body of a patient using a position tracking system, the medical instrument being configured to move within the body of the patient;
    (b) obtaining, based on preoperative image data, 3D data representative of at least a part of the body within a common frame of reference;

(c) receiving a start point and a termination point associated with the body;

(d) calculating, based on the 3D data, a 3D path of the medical instrument from the start point to the termination point;

(e) identifying, based on the 3D data, one or more turning points along the 3D path that exceed a curvature threshold; and (f) displaying, on a display screen, a virtual camera view comprising a virtual representation of the medical instrument relative to two-dimensional (2D) preoperative images, including respective 2D indications of a desired direction to the 3D path from the medical instrument.

13. The method according to claim 12, wherein the preoperative image data comprises 3D voxel data.

14. The method according to claim 13, wherein calculating of the 3D path of the medical instrument through the body further comprises calculating a Hounsfield Unit (HU) value for a set of voxels from the 3D voxel data.

15. The method according to claim 13, further comprising identifying, based on the 3D voxel data, one or more non-air sections along the 3D path, wherein the virtual camera view further comprises at least one visual cue associated with the non-air sections.

16. The method according to claim 13, wherein the virtual camera view further comprises a virtual endoscopic image, based on the 3D voxel data, of the body viewed from at least one respective location of at least one respective virtual camera including an animated representation of the medical instrument positioned in the virtual endoscopic image in accordance with the tracked coordinates, and a 3D indication of the direction to the 3D path from the medical instrument.

17. The method according to claim 12, further comprising identifying a point along the 3D path that is closest to the medical instrument and computing a 3D vector relative to the point and the tracked coordinates of the medical instrument, wherein the 2D indications are based on the 3D vector.

18. The method according to claim 12, further comprising providing for user selection a virtual camera view for each of the one or more turning points via the display screen, and wherein the displayed virtual camera view is based on the user selection.

19. The method according to claim 12, wherein the virtual camera view further comprises three respective 2D CT slices including three respective 2D indications of the direction.

20. A software product, comprising a non-transient computer readable medium in which program instructions are stored, which instructions, when read by a central processing unit (CPU), cause the CPU to:

(i) track coordinates of a medical instrument within a body of a patient using a position tracking system, the medical instrument being configured to move within the body of the patient;

(ii) obtain, based on preoperative image data, 3D data representative of at least a part of the body within a common frame of reference;

(iii) receive a start point and a termination point associated with the body;

(iv) calculate, based on the 3D data, a 3D path of the medical instrument from the start point to the termination point;

(v) identify, based on the 3D data, one or more turning points along the 3D path that exceed a curvature threshold; and (vi) display, on the display screen, a virtual camera view for one or more of the turning points comprising a virtual representation of the medical instrument relative to two-dimensional (2D) CT slices including respective 2D indications of a desired direction to the 3D path from the medical instrument.

* * * * *